(12) United States Patent
Goldstein et al.

(10) Patent No.: US 12,102,432 B2
(45) Date of Patent: Oct. 1, 2024

(54) USES OF TRANSDERMAL GLOMERULAR FILTRATION RATE MEASUREMENT IN CONTINUOUS RENAL REPLACEMENT THERAPY

(71) Applicant: MediBeacon Inc., St. Louis, MO (US)

(72) Inventors: Stuart L. Goldstein, Cincinnati, OH (US); Richard B. Dorshow, Creve Coeur, MO (US)

(73) Assignee: MEDIBEACON, INC., St. Louis, MO (US)

( * ) Notice: Subject to any disclaimer, the term of this patent is extended or adjusted under 35 U.S.C. 154(b) by 1342 days.

(21) Appl. No.: 16/552,609

(22) Filed: Aug. 27, 2019

(65) Prior Publication Data

US 2020/0187838 A1 Jun. 18, 2020

Related U.S. Application Data

(60) Provisional application No. 62/778,334, filed on Dec. 12, 2018.

(51) Int. Cl.
| | | |
|---|---|---|
| A61B 5/1455 | (2006.01) | |
| A61B 5/00 | (2006.01) | |
| A61B 5/145 | (2006.01) | |
| A61K 49/00 | (2006.01) | |

(52) U.S. Cl.
CPC ...... *A61B 5/14556* (2013.01); *A61B 5/14525* (2013.01); *A61B 5/4848* (2013.01); *A61K 49/0021* (2013.01)

(58) Field of Classification Search
None
See application file for complete search history.

(56) References Cited

U.S. PATENT DOCUMENTS

| | | |
|---|---|---|
| 8,115,000 B2 | 2/2012 | Rajagopalan et al. |
| 8,155,000 B2 | 4/2012 | Vasseur |
| 2003/0236452 A1 | 12/2003 | Melker et al. |
| 2006/0095102 A1 | 5/2006 | Perez |
| 2008/0281173 A1 | 11/2008 | Esenaliev et al. |
| 2011/0207161 A1 | 8/2011 | Anderberg et al. |
| 2013/0116512 A1 | 5/2013 | Imran |
| 2014/0107325 A1 | 4/2014 | Platzek et al. |
| 2015/0147277 A1 | 5/2015 | Dorshow et al. |
| 2015/0297819 A1* | 10/2015 | Szamosfalvi ....... A61M 1/3406 604/6.07 |
| 2015/0306486 A1 | 10/2015 | Logan et al. |
| 2018/0110881 A1 | 4/2018 | Dorshow et al. |
| 2019/0125901 A1 | 5/2019 | Debreczeny et al. |
| 2019/0125902 A1 | 5/2019 | Rajagopalan et al. |

FOREIGN PATENT DOCUMENTS

| | | |
|---|---|---|
| AU | 2013202655 B2 | 5/2013 |
| CN | 102246038 A | 11/2011 |
| CN | 103547573 A | 1/2014 |

OTHER PUBLICATIONS

Dorshow et al. Clinical study results of a real-time point-of-care glomerular filtration rate measurement. Nov. 3, 2017. MediBeacon Inc. Poster FR-PO750, Asn Kidney Week. (Year: 2017).*
Lu Jing et al., "Lian xu xing shen zang ti dai liao fa zai lao nian duo zang qi gong neng zhang ai zong he zheng zhong de ying yong," Fujian Med J, 3:56-58 (2008).
International Search Report for International Application No. PCT/US2019/048329, Issued on Nov. 7, 2019, 10 pages.
Churchwell et al., "Drug dosing during continuous renal replacement therapy", Seminars in Dialysis, Published Apr. 2009, vol. 22, pp. 185-188.
Rajagopalan et al., "Hydrophilic Pyrazine Dyes as Exogenous Fluorescent Tracer Agents for Real-Time Point-of-Care Measurement of Glomerular Filtration Rate", Journal of Medicinal Chemistry, Published Jun. 13, 2011, vol. 54, pp. 5048-5058.
Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.
Chinen et al., "Fluorescence-Enhanced Europium-Diethylenetriaminepentaacetic (DTPA)-Monoamide Complexes for the Assessment of Renal Function," J. Med. Chem., vol. 51, (2008), pp. 957-962.
Dean et al., "Inulin, Diodone, Creatinine And Urea Clearances in Newborn Infants," J. Physiol., vol. 106, (1947), pp. 431-439.
Debreczeny et al., "Transdermal Optical Renal Function Monitoring in Humans: Development, Verification, and Validation of a Prototype Device," Journal of Biomedical Optics, vol. 23, No. 5, (May 2018), pp. 057003-1-057003-9.
Friedman et al., "A comparison of the renal clearances of allantoin and inulin in man," Fed. Proc., vol. 7, No. 1 Pt 1, (1948), 1 page.
Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Med. (Chic), vol. 77, (1946), pp. 385-392.

(Continued)

*Primary Examiner* — Jennifer Chin
(74) *Attorney, Agent, or Firm* — Armstrong Teasdale LLP

(57) ABSTRACT

Disclosed herein is a method for determining a dosing prescription for a medicament in a patient undergoing CRRT. The method generally includes administering to the bloodstream of the patient a fluorescent agent; administering to the patient at least one dose of the medicament; performing CRRT on the patient after administering the fluorescent agent to the patient; exposing the fluorescent agent to visible or infrared light; monitoring transcutaneously a change in the spectral energy from the fluorescent agent over a period of time; correlating a change in intensity of the spectral energy from the fluorescent agent to a clearance rate of the fluorescent agent from the bloodstream in the patient; calculating a clearance rate of the medicament in the patient; determining an amount of the medicament in the bloodstream of the patient as a function of time; and adjusting a dosing prescription of the medicament to the patient.

14 Claims, 23 Drawing Sheets

(56) References Cited

OTHER PUBLICATIONS

Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.

Nagpal et al., "Combined Fluorescein, Indocyanine angiography and Optical Coherent Tomography Using Spectralis," Rajasthan Journal Of Ophthalmology, (2011), 8 pages.

Navar et al., "Distal Tubular Feedback in the Autoregulation of Single Nephron Glomerular Filtration Rate," J. Clin. Invest., vol. 53, (1974), pp. 516-525.

Nicholson et al., "Renal Function as Affected by Experimental Unilateral Kidney Lesions : I. Nephrosis Due to Iodium Rartrate," J. Exp. Med., vol. 68, (1938), pp. 439-456.

Pill et al., "Fluorescein-labeled Sinistrin as Marker of Glomerular Filtration Rate," European Journal of Medicinal Chemistry, vol. 40, (2005), pp. 1056-1061.

Poujeol et al., "Glomerular Filtration Rate and Microsphere Distributions in Single Nephron of Rat Kidney," Pflugers Arch., vol. 357, (1975), pp. 291-301.

Robson et al., "The Determination of the Renal Clearance of Inulin in Man," Q. J. Exp. Physiol., vol. 35, (1949), pp. 111-134.

Schock-Kusch et al., "Transcutaneous measurement of glomerular filtration rate using FITC-sinistrin in rats," Nephrol Dial Transplant, vol. 24, (2009), pp. 2997-3001.

Shannon et al., "The Renal Excretion of Inulin and Creatinine by the Anaesthetized Dog and the Pump-Lung-Kidney Preparation", J. Physiol., vol. 98, (1940), pp. 97-108.

Yu et al., "Rapid determination of renal filtration function using an optical ratiometric imaging approach," Am. J. Physiol. Renal. Physiol., vol. 292, (2007), pp. F1873-F1880.

International Search Report received for PCT Patent Application No. PCT/US2019/013784, mailed on May 7, 2019, 6 pages.

International Preliminary Report on Patentability received for PCT Patent Application No. PCT/US2019/013784, mailed on Jul. 30, 2020, 8 pages.

Berge et al., "Pharmaceutical Salts", Journal of Pharmaceutical Sciences, Jan. 1977, vol. 66, No. 1, pp. 1-19.

Bugaj et al., "Pre-clinical toxicity evaluation of MB-102, a novel fluorescent tracer agent for real-time measurement of glomerular filtration rate", Regulatory Toxicology and Pharmacology, vol. 72, No. 1, Feb. 26, 2015, pp. 26-38.

Ostermann et al., "Drug management in acute kidney disease—Report of the Acute Disease Quality Initiative XVI meeting", British Journal of Clinical Pharmacology, Blackwell Scientific Publ., GB vol. 84, No. 2, Dec. 1, 2017, pp. 396-403.

Trotman et al., "Antibiotic dosing in critically ill adult patients receiving continuous renal replacement therapy", Clinical Infectious Disease, The University of Chicago Press, Chicago, IL, vol. 41, No. 8 Oct. 15, 2005, pp. 1159-1166.

Ying Kuan et al., "Lack of effect of IGF-I on the glomerular filtration rate in non-diabetic patients with advanced chronic kidney disease", Growth Horm & IGF Res. 2009, vol. 19, pp. 219-225.

\* cited by examiner

USES OF TRANSDERMAL GLOMERULAR FILTRATION RATE MEASUREMENT IN CONTINUOUS RENAL REPLACEMENT THERAPY

CROSS REFERENCE TO RELATED APPLICATIONS

This application claims priority benefit of U.S. Provisional Application Ser. No. 62/778,334 filed Dec. 12, 2018, the entire contents of which are incorporated by reference herein.

FIELD OF INVENTION

The field of the disclosure relates generally to methods for monitoring the clearance of a fluorescent agent from the bloodstream of a patient. More specifically, the field of the disclosure generally relates to correlating the clearance of a fluorescent agent from the bloodstream of a patient to the clearance of at least one medicament from the bloodstream of a patient undergoing continuous renal replacement therapy (CRRT).

BACKGROUND

Acute kidney injury (AKI) is defined by the American Kidney Association as a sudden episode of kidney failure or kidney damage that happens within a few hours or a few days. AKI can result in the build-up of waste products in the bloodstream of a patient and can make it difficult or impossible for the kidneys to maintain the proper homeostatic fluid balance in the body. It can also affect other organs, such as the brain, heart and lungs, and is not uncommon in intensive care and older adults. One of the most important methods in treating AKI is the use of renal replacement therapy (RRT). There are no standard tests to determine if a patient needs RRT; the need is assessed using more generalized indications such as volume overload in the patient that does not respond to diuretic therapy, hyperkalemia and/or metabolic acidosis refractory to medical management, uremia with symptoms of encephalopathy, pericarditis or uremic bleeding, and intoxication with a drug that can be removed by dialysis.

With regard to conventional renal function measurement, an approximation of a patient's glomerular filtration rate (GFR), measured in units of mL/min/1.73 m$^2$, is made via a 24 hour urine collection procedure that typically requires (as the name suggests) about 24 hours for urine collection, several more hours for analysis, along with a meticulous bedside collection technique. Unfortunately, the undesirably late timing and significant duration of this conventional procedure can reduce the likelihood of effectively treating the patient and/or saving the kidney(s). However, this is not possible for a patient receiving CRRT. A patient undergoing CRRT does not have stable or normal kidney function, and, in severe cases of AKI, may have a GFR of <10 mL/min/1.73 m$^2$. Problematically, CRRT clears many small solutes, including lifesaving medicaments, from the bloodstream of the patient, so an accurate assessment of small solute clearance by CRRT is critical to optimize patient care.

| Stage | Description | GFR* |
|---|---|---|
| At increased risk | Increase of risk factors (e.g., diabetes, high blood pressure, family history, age, ethnicity) | >90 |

-continued

| Stage | Description | GFR* |
|---|---|---|
| 1 | Kidney damage with normal kidney function | >90 |
| 2 | Kidney damage with mild loss of kidney function | 60-89 |
| 3a | Mild to moderate loss of kidney function | 44-59 |
| 3b | Moderate to severe loss of kidney function | 30-44 |
| 4 | Severe loss of kidney function | 15-29 |
| 5 | Kidney failure; dialysis required | <15 |

*mL/min/1.73 m$^2$

Patients undergoing CRRT, regardless of the underlying cause, often have multiple medical conditions, both chronic and acute, requiring different types of treatment, and are receiving many different medicaments. CRRT is a filtering system known to remove some drugs from the bloodstream. Only rough estimates are possible to determine how much of a specific medicament is removed during CRRT in order to determine if additional doses or a different dosing prescription of the medicament are necessary. Thus, there is a need to determine the rate in which different medicaments are removed from the bloodstream of a patient undergoing CRRT in order to improve or adjust the dosing prescription for that medicament. Because patients are often receiving multiple different drugs, there is a need to determine the rate of clearance of each drug individually in a single test rather than performing a different test for each medicament.

Different CRRT modalities have several different parameters, and the different settings on each CRRT device determines how effectively and how quickly different medicaments are removed from the bloodstream of a patient. The same medicament may be removed at different rates based on different instrument settings. As such, it is extremely difficult to determine from one instrument to the next or one setting to the next how quickly a medicament is being removed from the bloodstream of a patient. Without this information, it is difficult for a medical professional to determine proper doses and dosing prescriptions for a specific medicament for a specific patient. Even different CRRT filters remove different medicaments at different rates. Thus, there is a need to determine the rate in which a medicament is being removed from the bloodstream of a patient that can be done independently of the settings on the CRRT instrument.

BRIEF DESCRIPTION

Disclosed herein is a method for determining a dosing prescription for a medicament in a patient undergoing CRRT. The method generally includes administering to the bloodstream of the patient a fluorescent agent; administering to the patient at least one dose of the medicament wherein administering the fluorescent agent and the medicament to the patient is either sequential or simultaneous; performing CRRT on the patient after administering the fluorescent agent to the patient; exposing the fluorescent agent to visible or infrared light, thereby causing spectral energy to emanate from the fluorescent agent; monitoring transcutaneously a change in the spectral energy from the fluorescent agent over a period of time; correlating a change in intensity of the spectral energy from the fluorescent agent to a clearance rate of the fluorescent agent from the bloodstream in the patient; calculating a clearance rate of the medicament in the patient based on the clearance rate of the fluorescent agent; determining an amount of the medicament in the bloodstream of the patient as a function of time based on the clearance rate of the medicament; and adjusting a dosing prescription of the medicament to the patient based on the amount of the medicament in the bloodstream of the patient as a function of time thereby determining the dosing prescription for the medicament to the patient.

In another aspect, disclosed herein is a method for monitoring a clearance rate of a medicament in a patient undergoing CRRT. The method generally includes administering to the bloodstream of the patient a fluorescent agent; administering to the patient at least one dose of the medicament wherein administering the fluorescent agent and the medicament to the patient is either sequential or simultaneous; performing CRRT on the patient after administering the fluorescent agent to the patient; exposing the fluorescent agent to visible or infrared light, thereby causing spectral energy to emanate from the fluorescent agent; monitoring transcutaneously a change in spectral energy from the fluorescent agent over a period of time; correlating a change in intensity of the spectral energy from the fluorescent agent to a clearance rate of the fluorescent agent from the bloodstream in the patient; calculating a clearance rate of the medicament in the patient to the clearance rate of the fluorescent agent; and determining an amount of the medicament in the bloodstream of the patient as a function of time based on the clearance rate of the medicament thereby monitoring the amount of the medicament in the bloodstream of the patient.

In still yet another aspect, disclosed herein is a method for determining if a patient undergoing CRRT is receiving a therapeutically effective dose of a medicament for a therapeutically effective time period. The method generally includes administering to the bloodstream of the patient a fluorescent agent; administering to the patient at least one dose of the medicament wherein administering the fluorescent agent and the medicament to the patient is either sequential or simultaneous; performing CRRT on the patient after administering the fluorescent agent to the patient; exposing the fluorescent agent to visible or infrared light, thereby causing spectral energy to emanate from the fluorescent agent; monitoring transcutaneously a change in spectral energy from the fluorescent agent over a period of time; correlating a change in intensity of the spectral energy from the fluorescent agent to a clearance rate of the fluorescent agent from the bloodstream in the patient; calculating a clearance rate of the medicament in the patient to the clearance rate of the fluorescent agent; determining a concentration of the medicament in the bloodstream of the patient as a function of time based on the clearance rate of the medicament thereby monitoring an amount of the medicament in the bloodstream of the patient as a function of time; and comparing the amount of the medicament in the bloodstream of the patient at a specific time point to a predetermined therapeutically effective concentration thereby determining if the patient is receiving a therapeutically effective dose of the medicament for a therapeutically effective time period.

Figure 1:
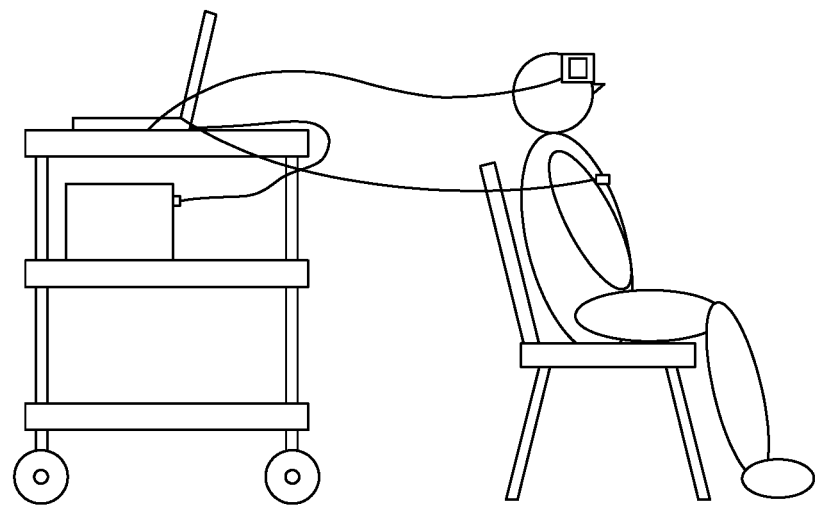
FIG. 1 illustrates a generalized system for a renal monitoring assembly in a patient.

Unless otherwise indicated, the drawings and figures provided herein illustrate features of embodiments of the disclosure or results of representative experiments illustrating some aspects of the subject matter disclosed herein. These features and/or results are believed to be applicable in a wide variety of systems including one or more embodiments of the disclosure. As such, the drawings are not intended to include all additional features known by those of ordinary skill in the art to be required for the practice of the embodiments, nor are they intended to be limiting as to possible uses of the methods disclosed herein.

DETAILED DESCRIPTION

In the following specification and the claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event or a circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

Definitions

As used herein, "CRRT" refers to continuous renal replacement therapy (CRRT). There are four types of CRRT: slow continuous ultra-filtration (SCUF), continuous venovenous hemofiltration (CVVH), continuous venovenous hemodialysis (CVVHD), and continuous venovenous hemodiafiltration (CVVHDF). All four types are encompassed herein unless context makes it clear that one specific type is referenced.

Different modalities of CRRT include the use of a replacement fluid, an effluent or both. For example, CVVH and CVVHDF use a replacement fluid while CVVHD uses a dialysis fluid. As used herein, the term "effluent" refers to any type of replacement fluid or effluent used with any CRRT modality. CRRT can be prescribed as continuous venovenous hemofiltration (all replacement fluid), continuous venovenous hemodialysis (all dialysis fluid) or continuous venovenous hemodiafiltration (a combination of replacement fluid and dialysis fluid). The specific modality of CRRT specifies the nature of the effluent. The term "effluent rate" refers to the flow rate for that specific effluent or combination of effluents in the CRRT modality in which it is utilized.

The terms "medicament", "medication", "medicine", "therapeutic agent" and "drug" are used interchangeably herein and describe a pharmaceutical composition or product intended for the treatment of a medical condition having at least one symptom. The pharmaceutical composition or product will have a physiological effect on the patient when it is introduced into the body of a patient. The pharmaceutical composition can be in any suitable formulation unless a specific formulation type is required or disclosed. In some instances, the medicament will be approved by the US FDA while in other instances it may be experimental (e.g., clinical trials) or approved for use in a country other than the United States (e.g., approved for use in China or Europe). In instances where these terms are used, it is understood that they refer to both singular and plural instances. In some embodiments herein, two or more medicaments may be used in a form of combination therapy. In all cases, the selection of the proper medicament (singular or plural) will be based on the medical condition of the patient and the assessment of the health care professional administering, supervising and/or directing the treatment of the patient.

An "effective amount" or a "therapeutically effective dose" in reference to a medicament is an amount sufficient to treat, ameliorate, or reduce the intensity of at least one symptom associated with the medical condition. In some aspects, an effective amount of a medicament is an amount sufficient to have a beneficial or desired clinical result including alleviation or reduction in one or more symptoms of a medical condition. In some aspects, an effective amount of the medicament is an amount sufficient to alleviate all symptoms of a medical condition.

As used herein, a "therapeutically effective time period" is a length of time required for a medicament to have a therapeutic effect on the patient. A therapeutically effective time period depends on the dose of the medicament because, in some instances, a higher dose of a medicament will have an effect faster than a lower dose.

The term "patient" as used herein refers to a warm blooded animal such as a mammal which is the subject of a medical treatment for a medical condition that causes at least one symptom. It is understood that at least humans, dogs, cats, and horses are within the scope of the meaning of the term. In some aspects, the patient is human.

As used herein, the term "body surface" refers to any desired surface of the body of a human or animal patient. Examples that may be mentioned include skin surfaces, surfaces of fingernails or toenails or other surfaces, more particularly surfaces exposed to the atmosphere. Non-limiting examples of body surfaces where a renal monitoring assembly may be placed include the ear lobe, sternum, chest, arm, leg, back, hand, foot, shoulder, hip, occipital triangle, and buttocks.

As used herein, the term "treat" or "treatment", or a derivative thereof, contemplates partial or complete amelioration of at least one symptom associated with the medical condition of the patient.

"Steady state" refers to the situation where the overall intake of a medicament is approximately in dynamic equilibrium with its elimination. Elimination of the medicament may be by any knowns means that reduces the concentration of the medicament in the bloodstream of the patient, including, but not limited to, renal filtration, hepatic metabolism and CRRT. In some aspects herein, the only way by which a medicament is eliminated from the patient is CRRT.

A discussion of various pharmacokinetic parameters and the methods of measuring and calculating them can be found in Clinical Pharmacokinetics and Pharmacodynamics: Concepts and Applications, M. Rowland and T. N. Tozer, (Lippincott, Williams & Wilkins, 2010) which is incorporated by reference for its teachings thereof.

In one aspect disclosed herein is a method for determining a dosing prescription for a medicament in a patient undergoing CRRT. The method generally includes: administering to the bloodstream of the patient a fluorescent agent; administering to the patient at least one dose of the medicament wherein administering the fluorescent agent and the medicament to the patient is either sequential or simultaneous; performing CRRT on the patient after administering the fluorescent agent to the patient; exposing the fluorescent agent to visible or infrared light, thereby causing spectral energy to emanate from the fluorescent agent; monitoring transcutaneously a change in the spectral energy from the fluorescent agent over a period of time; correlating a change in intensity of the spectral energy from the fluorescent agent to a clearance rate of the fluorescent agent from the bloodstream in the patient; calculating a clearance rate of the medicament in the patient based on the clearance rate of the fluorescent agent; determining an amount of the medicament in the bloodstream of the patient as a function of time based on the clearance rate of the medicament; and adjusting the dosing prescription of the medicament to the patient based on the amount of the medicament in the bloodstream of the patient as a function of time thereby determining the dosing prescription for the medicament to the patient.

In another aspect, disclosed herein is a method for monitoring a clearance rate of a medicament in a patient undergoing CRRT. The method generally includes: administering to the bloodstream of the patient a fluorescent agent; administering to the patient at least one dose of the medicament wherein administering the fluorescent agent and the medicament to the patient is either sequential or simultaneous; performing CRRT on the patient after administering the fluorescent agent to the patient; exposing the fluorescent agent to visible or infrared light, thereby causing spectral energy to emanate from the fluorescent agent; monitoring transcutaneously a change in spectral energy from the fluorescent agent over a period of time; correlating a change in intensity of the spectral energy from the fluorescent agent to a clearance rate of the fluorescent agent from the bloodstream in the patient; calculating a clearance rate of the medicament in the patient to the clearance rate of the fluorescent agent; and determining an amount of the medicament in the bloodstream of the patient as a function of time based on the clearance rate of the medicament thereby monitoring the amount of the medicament in the bloodstream of the patient.

In another aspect, disclosed herein is a method for determining if a patient undergoing CRRT is receiving a therapeutically effective dose of a medicament for a therapeutically effective time period. The method generally includes: administering to the bloodstream of the patient a fluorescent agent; administering to the patient at least one dose of the medicament wherein administering the fluorescent agent and the medicament to the patient is either sequential or simultaneous; performing CRRT on the patient after administering the fluorescent agent to the patient; exposing the fluorescent agent to visible or infrared light, thereby causing spectral energy to emanate from the fluorescent agent; monitoring transcutaneously a change in spectral energy from the fluorescent agent over a period of time; correlating a change in intensity of the spectral energy from the fluorescent agent to a clearance rate of the fluorescent agent from the bloodstream in the patient; calculating a clearance rate of the medicament in the patient to the clearance rate of the fluorescent agent; determining a concentration of the medicament in the bloodstream of the patient as a function of time based on the clearance rate of the medicament thereby monitoring the amount of the medicament in the bloodstream of the patient; and comparing the concentration of the medicament in the bloodstream of the patient at a specific time point to a predetermined therapeutically effective concentration. If the concentration at a specific time point is below the predetermined therapeutically effective concentration, then the patient is not receiving a therapeutically effective dose of a medicament at the time point. If the concentration at a specific time point is at or above the predetermined therapeutically effective concentration, then the patient is receiving a therapeutically effective dose of a medicament at the time point.

In some aspects, if the patient is not receiving a therapeutically effective dose of a medicament at the time point, then the method further includes administering at least one additional dose of the medicament to the patient.

As used herein, the term "clearance rate" or "clearance" is indicative of how quickly and/or efficiently waste products are removed from the bloodstream of the patient. It is also indicative of how quickly different medicaments are removed from the bloodstream of the patient. Because the kidneys of the patient undergoing CRRT are not filtering the blood, the patient does not have a GFR value with which to assess kidney function.

When monitoring the change in spectral energy from the fluorescent agent, a period of time will pass before the rate of change can be determined. At least two different time points are utilized in order to calculate the rate in which the spectral energy changes. As such, the period of time over which the change in spectral energy is monitored will affect the measurement of the clearance rate. If the period of time is too short, the data is less than optimal. If the time period is too long, the method becomes impractical for routine use. In some aspects the period of time is less than 1 minute, less than 2 minutes, less than 5 minutes, less than 10 minutes, less than 15 minutes, less than 30 minutes, less than 45 minutes, less than 60 minutes, less than 90 minutes, less than 120 minutes, less than 150 minutes, or less than 180 minutes. In some aspects, the time period is from 1 to 180 minutes. In some aspects, the time period is less than 3 hours, less than 6 hours, less than 12 hours, less than 18 hours, less than 24 hours, less than 36 hours, less than 48 hours, less than 60 hours, or less than 72 hours. In some aspects, the time period is such that the fluorescent agent is no longer detectable, and the detected spectral energy has returned to the baseline value.

As used herein, "adjusting a dosing prescription of the medicament" refers to changing at least one parameter associated with the administration of the medicament. By way of example and not limitation, one way in which the dosing prescription of the medicament is adjusted is to increase the amount and/or frequency of administering the medicament to the patient. By way of another nonlimiting example, for a drug administered intravenously, the time period over which the patient receives the medicament or the flow rate of the intravenous solution could be increased or decreased. By way of another nonlimiting example, for a drug administered intravenously, the concentration of the medicament in the intravenous solution may be increased or decreased. By way of another nonlimiting example, for a medicament administered orally, the patient could receive a different dose and/or be given the same dose either more or less frequently. Any other methods by which the dosing prescription of a medicament can be changed are envisioned and encompassed herein. In some instances, the patient is already receiving a therapeutically effective dose of the medicament, so no adjustment is necessary.

As used herein, "administering to the bloodstream of the patient a fluorescent agent" encompasses any known method by which the fluorescent agent can be administered to the patient where it reaches the bloodstream. Specific methods include, but are not limited to, intravenous administration, a bolus injection, oral administration, a suppository, subcutaneous injection, and intradermal injection. In some aspects, the fluorescent agent is administered by intravenous administration. In some aspects, the fluorescent agent is administered by bolus injection. In some aspects, the fluorescent agent is administered by oral administration. In some aspects, the fluorescent agent is administered as a suppository. In some aspects, the fluorescent agent is administered by subcutaneous injection. In some aspects, the fluorescent agent is administered by intradermal injection. The specific method of administration will be based on the medical needs and condition of the patient and selected by the health care professional administering, supervising and/or directing the treatment of the patient.

In some aspects, exposing the fluorescent agent to visible or infrared light includes: placing a renal monitoring assembly on the skin of the patient. In some aspects, the renal monitoring assembly is as described elsewhere herein.

CRRT Modalities

CRRT refers to several different modalities of blood filtering systems used for the treatment of patients: slow continuous ultra-filtration (SCUF), continuous venovenous hemofiltration (CVVH), continuous venovenous hemodialysis (CVVHD), and continuous venovenous hemodiafiltration (CVVHDF). The methods disclosed herein are suitable for use with all four systems. The specific CRRT modality used will be based on the medical condition of the patient and the assessment of the health care professional administering, supervising and/or directing the treatment of the patient.

SCUF refers to a modality for the removal of water from the patient's blood as it travels through a filter. It is designed to only remove excess water in a process known as ultra-filtration. The amount of water removed is generally not sufficient to remove accumulated wastes in patients having an AKI. The purpose of SCUF is to prevent or treat fluid volume overload in a patient when waste product removal and/or pH adjustment is not necessary.

CVVH refers to a modality for the removal of large amounts of water across the filter membrane for the purpose of removing waste from a patient's bloodstream. When large volumes of water are washed across the membrane, solutes are also transferred along with the water (convection). Hemofiltration is the removal of water over and above the surplus plasma water removed during ultrafiltration. To prevent hypovolemia, water removed during hemofiltration is given back before the blood is returned to the patient in an equivalent volume of a balanced solution, unless a net negative fluid removal is desired. This is referred to as replacement and uses a substitution solution. The blood pH is affected with a buffer contained in the substitution (i.e., replacement) solution, and convection is driven by the concentration differential between the blood and the substitution solution. It is primarily used when the removal of large molecular weight substances (e.g., proteins) is desirable, or the patient is exhibiting signs of uremia, pH imbalance and/or electrolyte imbalance.

CVVHD refers to a modality that uses an infusion of dialysis fluid (dialysate) into the filter canister which then surrounds the blood filled filter segments. Solutes that are small enough to fit through the membrane of the dialysis filter will move from an area of high concentration to low concentration (diffusion). The makeup of the dialysate determines which solutes are removed or added to the bloodstream of the patient. In order to remove solutes, the concentration of the solute in the dialysate is lower than the blood concentration. In order to give something to the patient, the concentration of the solute in the dialysate is higher than the blood. CVVHD removes wastes by diffusion, without the use of hemofiltration (replacement fluid). It may be administered with or without fluid removal from the patient. The blood pH is affected with a buffer contained in the dialysate, and the concentration differential between the blood and the dialysate drives the diffusion. It is primarily used for the removal of solutes from the blood of the patient while safely managing fluid levels. Key indications include uremia, pH imbalance and/or electrolyte imbalance.

CVVHDF refers to a modality that combines dialysis and hemofiltration. It includes both dialysate and replacement fluids and can be administered with or without fluid removal from the patient. The blood pH is affected with a buffer contained in the dialysate and substitution solution. The concentration differential between the blood and the dialysate and substitution solutions drive waste removal (both convective and diffusive). It is most often used when the removal of large molecular weight molecules (e.g., proteins) is desired although small molecules (e.g., urea) can also be removed. Key indications include uremia, pH imbalance and/or electrolyte imbalance.

In all modalities of CRRT, blood is drawn from the patient into the CRRT apparatus, processed according to the medical needs of the patient and the capabilities of the CRRT apparatus, and then returned to the patient. The blood flow rate is determined by the medical needs of the patient and the type of modality being used. In some aspects, the blood flow rate is about 25 mL/min, about 50 mL/min, about 75 mL/min, about 100 mL/min, about 125 mL/min, about 150 mL/min, about 175 mL/min, about 200 mL/min, about 225 mL/min, about 250 mL/min, about 275 mL/min, or about 300 mL/min. In yet another aspect, the blood flow rate in the CRRT modality is between about 25 mL/min and 400 mL/min, between about 50 mL/min and 350 mL/min, or between about 50 mL/min and 350 mL/min.

In CRRT modalities that use an effluent, the effluent flow rate is one factor that affects the efficiency of the process and the rate in which waste products are removed from the blood of the patient. In some aspects, the flow rate of the effluent is about 5 mL/kg/hr, about 10 mL/kg/hr, about 15 mL/kg/hr, about 20 mL/kg/hr, about 25 mL/kg/hr, about 30 mL/kg/hr, about 35 mL/kg/hr, about 40 mL/kg/hr, about 45 mL/kg/hr, about 50 mL/kg/hr, about 55 mL/kg/hr, about 60 mL/kg/hr, about 75 mL/kg/hr, or about 100 mL/kg/hr. In yet another aspect, the flow rate of the effluent is between about 5 mL/kg/hr and 100 mL/kg/hr, between about 10 mL/kg/hr and 50 mL/kg/hr, or between about 25 mL/kg/hr and 40 mL/kg/hr. In some aspects, the effluent flow rate for an adult patient (i.e., 18 years or older) is from about 25 to 40 mL/kg/hr. The flow rate of the effluent will be selected based on the medical condition of the patient and the assessment of the health care professional administering, supervising and/or directing the treatment of the patient.

In some instances, children require CRRT. When administered to a child, in CRRT modalities that use an effluent, the flow rate of the effluent is about 500 mL/1.73 $m^2$/hr, about 1000 mL/1.73 $m^2$/hr, about 1500 mL/1.73 $m^2$/hr, about 2000 mL/1.73 $m^2$/hr, about 2500 mL/1.73 $m^2$/hr, about 3000 mL/1.73 $m^2$/hr, about 3500 mL/1.73 $m^2$/hr, or about 4000 mL/1.73 $m^2$/hr. In yet another aspect, the flow rate of the effluent is between about 500 mL/1.73 $m^2$/hr and about 4000 mL/1.73 $m^2$/hr, or about 2000 mL/1.73 $m^2$/hr and about 3000 mL/1.73 m²/hr. In some aspects, for a child under 18 years old and weighing less than about 70 kg, the effluent flow rate is from about 2000 to about 3000 mL/1.73 m²/hr. As used herein, a child is younger than 18 years old and weighs less than about 70 kg.

Fluorescent Agents

Suitable fluorescent molecules for use with the methods described herein are disclosed in U.S. Pat. No. 8,115,000 and U.S. 62/577,951, both of which are incorporated by reference in their entirety for all purposes. In some aspects, the fluorescent agent is eliminated from the body of a patient by glomerular filtration. In some aspects, the fluorescent agent is eliminated from the body of a patient only by glomerular filtration.

In some aspects, the fluorescent agent is a pyrazine derivative of Formula I, or a pharmaceutically acceptable salt thereof,

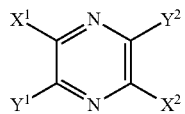

Formula I wherein each of $X^1$ and $X^2$ is independently —CN, —CO$_2$R$^1$, —CONR$^1$R$^2$, —CO(AA), —CO(PS) or —CONH(PS); each of $Y^1$ and $Y^2$ is independently selected from the group consisting of —NR$^1$R$^2$ and

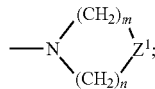

$Z^1$ is a single bond, —CR$^1$R$^2$—, —O—, —NR$^1$—, —NCOR$^1$—, —S—, —SO—, or —SO$_2$—; each of R$^1$ to R$^2$ are independently selected from the group consisting of H, —CH$_2$(CHOH)$_a$H, —CH$_2$(CHOH)$_a$CH$_3$, —CH$_2$(CHOH)$_a$CO$_2$H, —(CHCO$_2$H)$_a$CO$_2$H, —(CH$_2$CH$_2$O)$_c$H, —(CH$_2$CH$_2$O)$_c$CH$_3$, —(CH$_2$)$_a$SO$_3$H, —(CH$_2$)$_a$SO$_3^-$, —(CH$_2$)$_a$SO$_2$H, —(CH$_2$)$_a$SO$_2^-$, —(CH$_2$)$_a$NHSO$_3$H, —(CH$_2$)$_a$NHSO$_3^-$, —(CH$_2$)$_a$NHSO$_2$H, —(CH$_2$)$_a$NHSO$_2^-$, —(CH$_2$)$_a$PO$_4$H$_3$, —(CH$_2$)$_a$PO$_4$H$_2^-$, —(CH$_2$)$_a$PO$_4$H$^{2-}$, —(CH$_2$)$_a$PO$_4^{3-}$, —(CH$_2$)$_a$PO$_3$H$_2$, —(CH$_2$)$_a$PO$_3$H$^-$, and —(CH$_2$)$_a$PO$_3^{2-}$; (AA) comprises one or more amino acids selected from the group consisting of natural and unnatural amino acids, linked together by peptide or amide bonds and each instance of (AA) may be the same or different than each other instance; (PS) is a sulfated or non-sulfated polysaccharide chain that includes one or more monosaccharide units connected by glycosidic linkages; and 'a' is a number from 0 to 10, 'c' is a number from 1 to 100, and each of 'm' and 'n' are independently a number from 1 to 3. In another aspect, 'a' is a number from 1 to 10. In still yet another aspect, 'a' is 0, 1, 2, 3, 4, 5, 6, 7, 8, 9 or 10.

(AA) comprises one or more natural or unnatural amino acids linked together by peptide or amide bonds. The peptide chain (AA) may be a single amino acid, a homopolypeptide chain or a heteropolypeptide chain, and may be any appropriate length. In some embodiments, the natural or unnatural amino acid is an α-amino acid. In yet another aspect, the α-amino acid is a D-α-amino acid or an L-α-amino acid. In a polypeptide chain that includes two or more amino acids, each amino acid is selected independently of the other(s) in all aspects, including, but not limited to, the structure of the side chain and the stereochemistry. For example, in some embodiments, the peptide chain may include 1 to 100 amino acid(s), 1 to 90 amino acid(s), 1 to 80 amino acid(s), 1 to 70 amino acid(s), 1 to 60 amino acid(s), 1 to 50 amino acid(s), 1 to 40 amino acid(s), 1 to 30 amino acid(s), 1 to 20 amino acid(s), or even 1 to 10 amino acid(s). In some embodiments, the peptide chain may include 1 to 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s). In some embodiments, the amino acid is selected from the group consisting of D-alanine, D-arginine D-asparagine, D-aspartic acid, D-cysteine, D-glutamic acid, D-glutamine, glycine, D-histidine, D-homoserine, D-isoleucine, D-leucine, D-lysine, D-methionine, D-phenylalanine, D-proline, D-serine, D-threonine, D-tryptophan, D-tyrosine, and D-valine. In some embodiments, the α-amino acids of the peptide chain (AA) are selected from the group consisting of arginine, asparagine, aspartic acid, glutamic acid, glutamine, histidine, homoserine, lysine, and serine. In some embodiments, the α-amino acids of the peptide chain (AA) are selected from the group consisting of aspartic acid, glutamic acid, homoserine and serine. In some embodiments, the peptide chain (AA) refers to a single amino acid (e.g., D-aspartic acid or D-serine).

(PS) is a sulfated or non-sulfated polysaccharide chain including one or more monosaccharide units connected by glycosidic linkages. The polysaccharide chain (PS) may be any appropriate length. For instance, in some embodiments, the polysaccharide chain may include 1 to 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose). In yet another aspect, the polysaccharide chain is an amino sugar where one or more of the hydroxy groups on the sugar has been replaced by an amine group. The connection to the carbonyl group can be either through the amine or a hydroxy group.

In any aspect of the pyrazine compound of Formula I, one or more atoms may alternatively be substituted with an isotopically labelled atom of the same element. For example, a hydrogen atom may be isotopically labelled with deuterium or tritium; a carbon atom may be isotopically labelled with $^{13}$C or $^{14}$C; a nitrogen atom may be isotopically labelled with $^{14}$N or $^{15}$N. An isotopic label may be a stable isotope or may be an unstable isotope (i.e., radioactive). The pyrazine molecule may contain one or more isotopic labels. The isotopic label may be partial or complete. For example, a pyrazine molecule may be labeled with 50% deuterium thereby giving the molecule a signature that can be readily monitored by mass spectroscopy or other techniques. As another example, the pyrazine molecule may be labeled with tritium thereby giving the molecule a radioactive signature that can be monitored both in vivo and ex vivo using techniques known in the art.

In some aspects, the fluorescent agent is (2R,2'R)-2,2'-((3,6-diaminopyrazine-2,5-dicarbonyl)bis(azanediyl))bis(3-hydroxypropanoic acid) (also known as MB-102 or 3,6-diamino-N2,N5-bis(D-serine)-pyrazine-2,5-dicarboxamide)

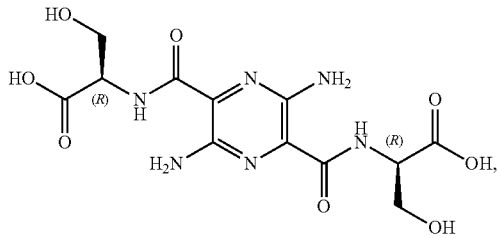

or a pharmaceutically acceptable salt thereof.

In some aspects, the fluorescent agent is (2S,2'S)-2,2'-((3,6-diaminopyrazine-2,5-dicarbonyl)bis(azanediyl))bis(3-hydroxypropanoic acid) (also known as 3,6-diamino-N2,N5-bis(L-serine)-pyrazine-2,5-dicarboxamide)

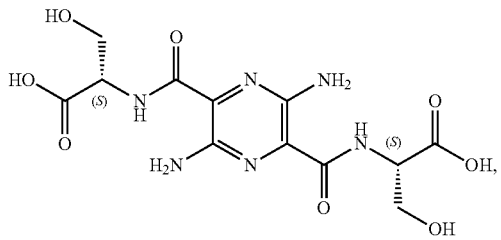

or a pharmaceutically acceptable salt thereof.

In still yet another aspect, the fluorescent agent is selected from the group consisting of acridines, acridones, anthracenes, anthracylines, anthraquinones, azaazulenes, azo azulenes, benzenes, benzimidazoles, benzofurans, benzoindocarbocyanines, benzoindoles, benzothiophenes, carbazoles, coumarins, cyanines, dibenzofurans, dibenzothiophenes, dipyrrolo dyes, flavones, imidazoles, indocarbocyanines, indocyanines, indoles, isoindoles, isoquinolines, naphthacenediones, naphthalenes, naphthoquinones, phenanthrenes, phenanthridines, phenanthridines, phenoselenazines, phenothiazines, phenoxazines, phenylxanthenes, polyfluorobenzenes, purines, pyrazines, pyrazoles, pyridines, pyrimidones, pyrroles, quinolines, quinolones, rhodamines, squaraines, tetracenes, thiophenes, triphenyl methane dyes, xanthenes, xanthones, and derivatives thereof.

Pharmaceutically acceptable salts are known in the art. In any aspect herein, the compound of Formula I may be in the form of a pharmaceutically acceptable salt. By way of example and not limitation, pharmaceutically acceptable salts include those as described by Berge, et al. in *J Pharm. Sci.*, 66(1), 1 (1977), which is incorporated by reference in its entirety for its teachings thereof. The salt may be cationic or anionic. In some embodiments, the counter ion for the pharmaceutically acceptable salt is selected from the group consisting of acetate, benzenesulfonate, benzoate, besylate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, triethiodide, adipate, alginate, aminosalicylate, anhydromethylenecitrate, arecoline, aspartate, bisulfate, butylbromide, camphorate, digluconate, dihydrobromide, disuccinate, glycerophosphate, jemisulfate, judrofluoride, judroiodide, methylenebis(salicylate), napadisylate, oxalate, pectinate, persulfate, phenylethylbarbarbiturate, picrate, propionate, thiocyanate, tosylate, undecanoate, benzathine, chloroprocaine, choline, diethanolamine, ethylenediamine, meglumine, procaine, benethamine, clemizole, diethylamine, piperazine, tromethamine, aluminum, calcium, lithium, magnesium, potassium, sodium zinc, barium and bismuth. Any functional group in the fluorescent agent capable of forming a salt may optionally form one using methods known in the art. By way of example and not limitation, amine hydrochloride salts may be formed by the addition of hydrochloric acid to the pyrazine. Phosphate salts may be formed by the addition of a phosphate buffer to the pyrazine. Any acid functionality present, such as a sulfonic acid, a carboxylic acid, or a phosphonic acid, may be deprotonated with a suitable base and a salt formed. Alternatively, an amine group may be protonated with an appropriate acid to form the amine salt. The salt form may be singly charged, doubly charged or even triply charged, and when more than one counter ion is present, each counter ion may be the same or different than each of the others.

Patients undergoing CRRT often suffer from a variety of medical conditions, including, but not limited to chronic kidney disease (CKD), acute kidney injury (AKI), acute renal failure, multiple organ failure, cardiac insufficiency and edema, acute pancreatitis, fulminant hepatitis, and liver failure. Because of this, they are generally administered a large array of one or more medicaments to treat the symptoms associated therewith. Any medicament useful in treating patients undergoing CRRT is encompassed herein. Examples of known medicaments useful in treating patients undergoing CRRT include, but are not limited to, antibiotics, anticoagulants, anticonvul sants, antifungals, antineoplastic agents, antipsychotics, antivirals, immunosuppressants, muscle relaxants, sedatives and vasoactive medicaments (e.g. inotropes, vasodilators, vasoconstrictors). In some aspects, the patient is receiving at least one antibiotic. In some aspects, the patient is receiving at least one anticoagulant. In some aspects, the patient is receiving at least one antifungal. In some aspects, the patient is receiving at least one antineoplastic agent. In some aspects, the patient is receiving at least one antipsychotic. In some aspects, the patient is receiving at least one antiviral. In some aspects, the patient is receiving at least one immunosuppressant. In some aspects, the patient is receiving at least one muscle relaxant. In some aspects, the patient is receiving at least one sedative. In some aspects, the patient is receiving at least one vasoactive medicament.

In some aspects where the patient is receiving at least one antibiotic, the at least one antibiotic is selected from the group consisting of acyclovir, amikacin, amoxicillin, amphotericin B, ampicillin, aztreonam, cefazolin, cefepime, cefotaxime, cefotetan, cefoxitin, ceftaroline, ceftazidime, ceftriaxone, cefuroxime, ciprofloxacin, clindamycin, daptomycin, doripenem, ertapenem, fluconazole, foscavir, ganciclovir, gentamicin, imipenem, levofloxacin, linezolid, meropenem, methicillin, moxifloxacin, nafcillin, oseltamivir, piperacillin, rifampin, sulbactam, tazobactam, telavancin, tigecycline, tobramycin, trimethoprim, vancomycin and combinations thereof.

In some aspects, the patient is receiving two or more medicaments. In some aspects, the patient is receiving three or more medicaments. In some aspects, the patient is receiving two or more medicaments from the same class of medicament. For example, a patient may receive two different antibiotics. In some aspects, the patient is receiving two or medicaments from different classes of medicaments. For example, a patient may receive an antibiotic and an anticoagulant. In some aspects, the medicament is eliminated from the bloodstream of the patient by renal clearance. In some aspects, the medicament is eliminated from the bloodstream of the patient only by renal clearance.

In some aspects the fluorescent agent is administered simultaneously with the at least one medicament. In some aspects, the fluorescent agent is administered sequentially with the at least one medicament. For sequential administration, either the fluorescent agent or the medicament is administered first. The time period between administration of the fluorescent agent and the medicament is any time period that is convenient for the health care provider administering the agents and still permits the use of the methods disclosed herein. In some aspects, the time period between administering the two agents is less than 1 minute, less than 5 minutes, less than 15 minutes, less than 30 minutes, less than 60 minutes, less than 2 hours, less than 5 hours, less than 12 hours, less than 24 hours, less than 36 hours, or less than 48 hours. In some aspects, the time period between administering the two agents is between 1 minute and 48 hours. Simultaneous as used herein uses the literal definition. For example, the fluorescent agent and the medicament are combined in a single dosage form (e.g., an IV or bolus injection) and administered as a single unit.

Renal Monitoring Assembly

One suitable system that includes a renal monitoring assembly for use with the methods described herein is disclosed in U.S. application Ser. No. 16/171,689, which is incorporated by reference in its entirety for all purposes.

Figure 2:
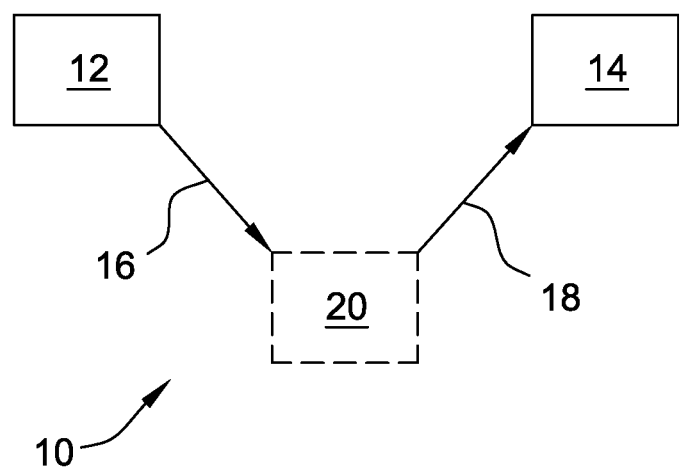
FIG. 2 illustrates a generalized system for renal monitoring assembly in a patient.

One generalized example of an in vivo renal monitoring assembly 10 that is suitable for use with, for example—human patients, is shown in FIGS. 1 and 2 and includes a light source 12 and a data processing system 14. The light source 12 generally includes or is interconnected with an appropriate device for exposing at least a portion of a patient's body to light therefrom. Examples of appropriate devices that may be interconnected with or be a part of the light source 12 include, but are not limited to, catheters, endoscopes, fiber optics, ear clips, hand bands, head bands, forehead sensors, surface coils, and finger probes. Indeed, any of a number of devices capable of emitting visible and/or near infrared light of the light source may be employed in the renal monitoring assembly 10. In one aspect, the light sources are LEDs where one of the LEDs emits light near the absorbance maximum of the fluorescent agent while the second LED emits light near the fluorescence emission maximum of the fluorescent agent. For example, one LED emits light at 450 nm while the second LED emits light at 560 nm.

Still referring to FIGS. 1 and 2, the data processing system 14 of the renal monitoring assembly may be any appropriate system capable of detecting spectral energy and processing data indicative of the spectral energy. For instance, the data processing system 14 may include one or more lenses (e.g., to direct and/or focus spectral energy), one or more filters (e.g., to fitter out undesired wavelengths of spectral energy), a photodiode or photomultiplier (e.g., to collect the spectral energy and convert the same into electrical signal indicative of the detected spectral energy), an amplifier (e.g., to amplify electrical signal from the photodiode or photomultiplier), and a processing unit (e.g., to process the electrical signal from the photodiode or photomultiplier). The data processing system 14 is preferably configured to manipulate collected spectral data and generate an intensity/time profile and/or a concentration/time curve indicative of renal clearance of a fluorescent agent of the present disclosure from patient 20. Indeed, the data processing system 14 may be configured to generate appropriate renal function data by comparing differences in manners in which normal and impaired cells remove the fluorescent agent from the bloodstream, to determine a rate or an accumulation of the fluorescent agent in organs or tissues of the patient 20, and/or to provide tomographic images of organs or tissues having the fluorescent agent associated therewith.

By way of example and not limitation, in one aspect the system comprises two silicon photomultipliers. The first photomultiplier includes a long pass filter while the second photomultiplier is unfiltered. This arrangement permits both the fluorescence emission and diffuse reflectance at the excitation and emission wavelengths to be measured. In one such embodiment, the fluorescence and diffuse reflectance measurement are combined into an Intrinsic Fluorescence measurement that is compensated for variations in tissue optical properties.

In some aspects of the methods disclosed herein, an effective amount of a fluorescent agent is administered to a patients in need thereof (e.g., in the form for a pharmaceutically acceptable composition). At least a portion of the body of the patient 20 is exposed to visible and/or near infrared light from the light source 12 as indicated by arrow 16. For instance, the light from the light source 12 may be delivered via a fiber optic that is affixed to an ear of the patient 20. The patient may be exposed to the light from the light source 12 before or after administration of the fluorescent agent to the patient 20. In some cases, it may be beneficial to generate a background or baseline reading of light being emitted from the body of the patient 20 (due to exposure to the light from the light source 12) before administering the fluorescent agent to the patient 20. When the fluorescent agent that is in the body of the patient 20 is exposed to the light from the light source 12, the fluorescent agent emanates light (indicated by arrow 18) that is detected/collected by the data processing system 14. Initially, administration of the fluorescent agent to the patient 20 generally enables an initial spectral signal indicative of the initial content of the fluorescent agent in the patient 20. The spectral signal then tends to decay as a function of time as the fluorescent agent is cleared from the patient 20. This decay in the spectral signal as a function of time is indicative of the patient's renal function. Additionally, if the fluorescent agent is injected into the vascular space of a patient, the initial kinetics reflect the equilibration of the fluorescent agent into the entire extracellular space of the patient. In some aspects, this equilibration is complete in less than 2 hours.

EXAMPLES

Absorption of MB-102

As an initial step, it was determined if the compound MB-102 adsorbs onto the hemodiafilter, tubing or other parts of the CRRT instrument. This study used a continuous venovenous hemofiltration (CVVH) configuration to assess MB-102 adsorptive clearance with a previously validated in vitro CVVH model using 1 L of pH regulated, citrate-anticoagulated bovine blood. Using a Braun DIAPACT™ CRRT system, two different hemodiafilters were tested: the HF1400 and the M150 hemodiafilters. New bovine blood, hemodiafilters, and CRRT tubing sets were used in each experiment. The blood was continuously stirred and maintained at 37° C. in a water bath during all experiments. Reconstituted MB-102 was added to the blood to achieve a final concentration of ~6.2 mg/L. Urea was used as a control and added to the blood to produce a blood urea nitrogen (BUN) concentration of ~75 mg/dL. Blood flow rates of 200 mL/min with an ultrafiltration rate ($Q_{uf}$) of 33 mL/min were tested. This maximized MB-102 contact with the membranes, both on the blood side and via convection through the hemodiafilter membrane. A closed system was developed to maintain a constant volume in the extracorporeal system. The effluent was used as the replacement fluid which was returned to the blood as a post-filter replacement fluid to maintain a constant blood volume. The CRRT instrument was primed with normal saline before operation, consequently the urea and MB-102 dilution caused by the residual priming solution was accounted for. Blood samples were collected from the pre-filter port at 0 (baseline), 5 (at which time mixing was complete), 10, 20, 30, and 60 minutes. Each experiment was repeated six times with new hemodiafilters and tubing sets.

Equations used to calculate the dilution factor and adsorption are as follows:

$$\% \text{ Adsorption} = \left(\frac{C_0 - C_{60}}{C_0} * 100\right) - \text{Dilution factor} \quad \text{Equation (1)}$$

wherein $C_0$ is the concentration of MB-102 in the pre-filter at time=0 minutes; and $C_{60}$ is the concentration of MB-102 in the pre-filter at time=60 minutes.

$$\% \text{ Dilution factor} = \frac{[Urea_0] - [Urea_{60}]}{[Urea_0]} * 100 \quad \text{Equation (2)}$$

where $[Urea_0]$ is the urea concentration in the pre-filter at time=0 minutes; and $[Urea_{60}]$ is the urea concentration in the pre-filter at time=60 minutes.

Continuous Hemofiltration (CVVH)

Figure 5:
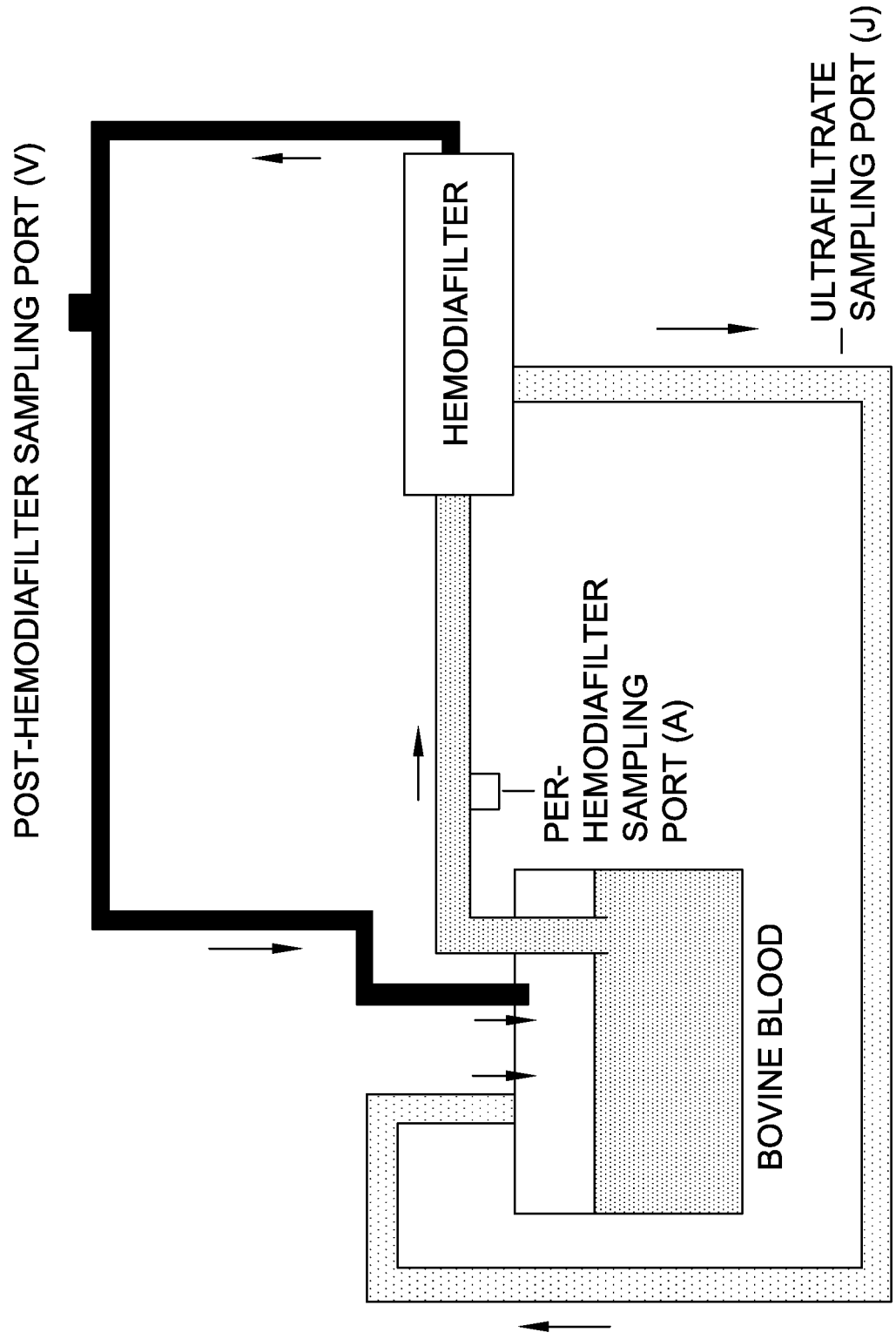
FIG. 5 is a schematic for a model ex vivo continuous venovenous hemofiltration (CVVH) system.

The procedure for the CVVH study was conducted using the model CVVH system illustrated in FIG. 5. The $CL_{TM}$ of urea and MB-102 were evaluated with different blood flow rates, ultrafiltration rate ($Q_{uf}$) and hemodiafilters (Table 1). In a closed-loop system, the formed effluent was returned to the blood as a post-filter replacement fluid downstream from the post-hemodiafilter blood sampling port. Pre- and post-hemodiafilter blood samples, and effluent samples were collected concurrently. Six experiments were conducted for each hemodiafilter, and new hemodiafilters and CRRT apparatus were used for each experiment. Sieving coefficient ($S_C$) and $CL_{TM}$ were calculated as follows:

$$S_C = \frac{C_{UF}}{(C_a + C_v)/2} \quad \text{Equation (3)}$$

where $S_c$ is the sieving coefficient; $C_{uf}$ is the concentration in the effluent; $C_a$ is the concentration of the solute in the pre-filter; and $C_v$ is the concentration of the solute in the post-filter.

$$CL_{conv} = S_C \times Q_{UF} \quad \text{Equation (4)}$$

wherein $CL_{conv}$ is the convective clearance for the post-filter replacement; $Q_{UF}$ is the ultrafiltration rate.

Continuous Hemodialysis (CVVHD)

Figure 6:
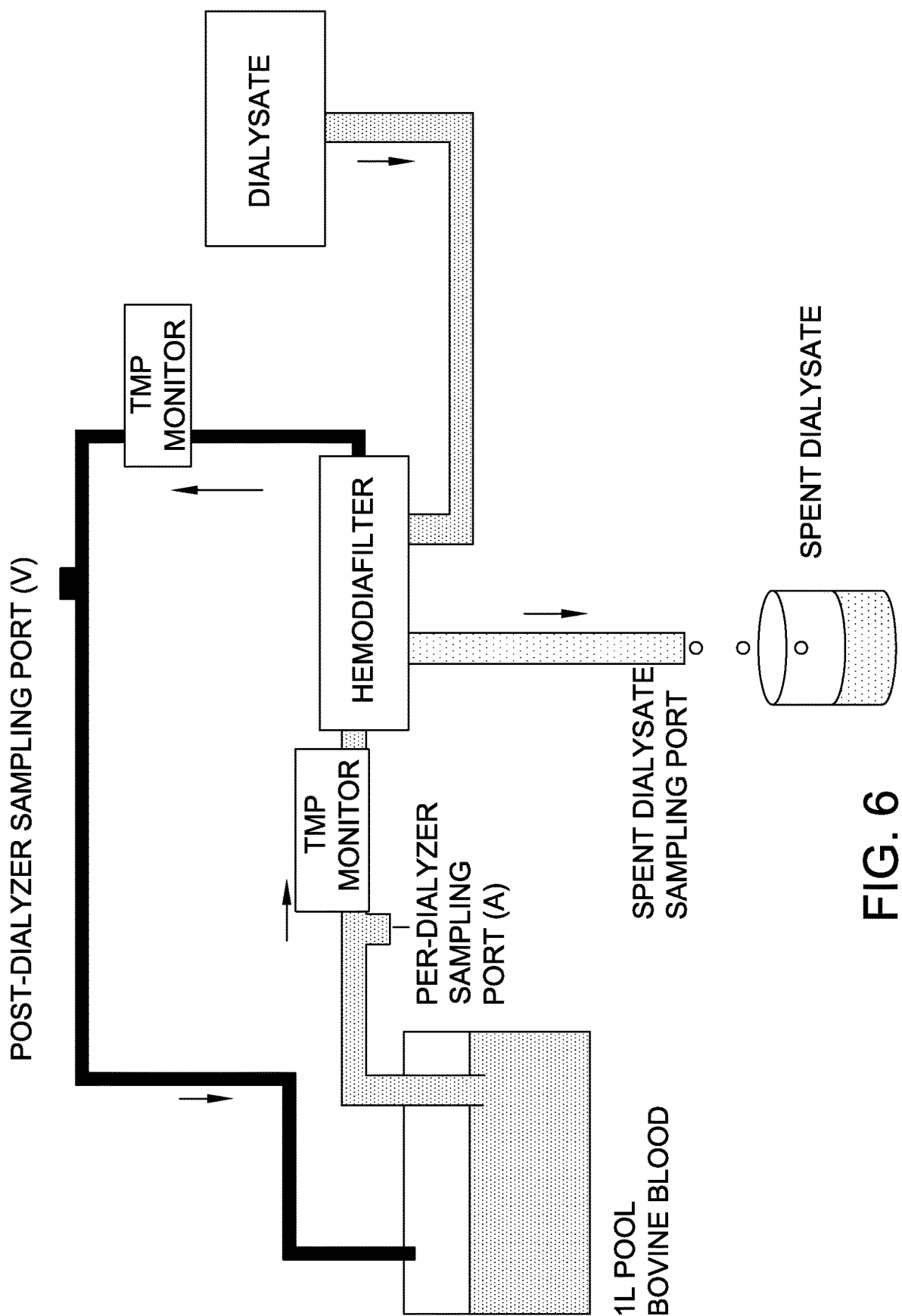
FIG. 6 is a schematic for a model ex vivo continuous venovenous hemodiafiltration (CVVHD) system.

For CVVHD experiments, the $CL_{TM}$ was assessed using a previously validated in vitro CVVHD model as illustrated in FIG. 6. Commonly used effluent flow rates of 16, 33, 50, and 100 mL/min, and a blood flow rate of 200 mL/min were used. Effluent was prepared according to directions from the manufacturer by mixing sodium bicarbonate powder (NATURALYTE® 4000, Fresenius Medical Care, Waltham, Mass., USA) with distilled water in a 45:1 ratio. After adding MB-102 and urea to the blood, it was recirculated through the circuit for 5 min for uniform coating of the extracorporeal circuit. A single-pass mode of the CVVHD procedure with four different flow rates was run in random order for each hemodiafilter. Blood samples were collected from the pre- and post-filter ports, and spent effluent samples were taken from the effluent port 5 min after initiation of the CVVHD experiments at all four effluent flow rates. These experiments were conducted on 6 new hemodiafilters and CRRT tubing sets. Saturation coefficient ($S_A$) and $CL_{TM}$ were calculated as follows:

$$S_A = \frac{C_{UF}}{(C_a + C_v)/2} \quad \text{Equation (5)}$$

$$CL_{diff} = (S_A \times Q_d) \quad \text{Equation (6)}$$

where $S_A$ is the saturation coefficient; $C_{UF}$ is the concentration in the effluent; $C_a$ is the concentration of the solute in the pre-filter; $C_V$ is the concentration of the solute in the post-filter; $CL_{diff}$ is the diffusion clearance for post-filter replacement; $Q_d$ is the effluent flow rate.

The clearance rate of a medicament and the clearance rate of the fluorescent agent are determined based on numerous factors, including, but not limited to, the age and health of the patient and the settings of the CRRT modality used to treat the patient. Because of this variability, in some aspects, these values are normalized to provide a comparative value that is more consistent from patient to patient and among different CRRT modalities. In some aspects, the clearance rates of the medicament and the fluorescent agent are used to calculate a clearance coefficient for the medicament. The clearance coefficient for a medicament is defined as the clearance rate of the medicament divided by the clearance rate of the fluorescent agent. A clearance coefficient of 1 indicates that the medicament and the fluorescent agent are removed from the body of the patient by that CRRT modality at the same rate, while a clearance coefficient less than 1 indicates that the medicament is removed from the body of the patient by CRRT at a slower rate than the fluorescent agent. This may happen when, for example, the medicament is more tightly bound to proteins in the bloodstream than the fluorescent agent.

Sample Analysis

All blood samples were collected and centrifuged at 3000 rpm for 10 minutes. The plasma and effluent samples were transferred to cryovials in duplicate and stored at −80° C. until analysis. BUN concentrations were analyzed with Advia 1800 (Siemens Healthcare Diagnostic Inc., Tarrytown, N.Y., USA) having a lower limit of quantification of 5 mg/dL.

Data Analysis

A power analysis calculation indicated that six experiments were required to detect a 25% difference in the extent of MB-102 adsorption. Similarly, six CVVH and CVVHD experiments with each hemodiafilter were used to detect a 25% difference in MB-102 $CL_{TM}$ between hemodiafilters. Assumptions used in these calculations included: a power of 90% and a standard deviation of 10% with a significance level of $p<0.05$. A two-tailed, unpaired t-test was used to compare differences between the two hemodiafilters, and the analysis of variance was used to compare different $Q_{UF}$ and $Q_d$ within each hemodiafilter type.

Results

Adsorption

The percent changes of urea and MB-102 concentrations from initial concentrations to the end of each study concentrations (60 min) are shown in Table 1. The mean percent changes with HF1400 hemodiafilters for MB-102 (18.7%) and urea (19.5%) were similar (p-value=0.9). The mean percent changes with M150 hemodiafilters for MB-102 (18.9%) and urea (19.3%) were also similar (p-value=0.8). Since urea is not adsorbed by the CRRT apparatus or hemodiafilters, the decrease in concentrations of MB-102 is considered to be a dilution from the priming solution. As a result, MB-102 adsorption to CRRT materials was not observed.

TABLE 1

The percent change at the end of each experiment for urea and MB-102

| Filter Type Experiment | HF1400 | | M150 | |
|---|---|---|---|---|
| Number | MB-102 (%) | Urea (%) | MB-102 (%) | Urea (%) |
| 1 | 9.9 | 19.6 | 10.5 | 18.0 |
| 2 | 11.1 | 20.0 | 28.5 | 17.0 |
| 3 | 25.8 | 18.2 | 22.8 | 22.0 |

TABLE 1-continued

The percent change at the end of each experiment for urea and MB-102

| Filter Type Experiment | HF1400 | | M150 | |
|---|---|---|---|---|
| Number | MB-102 (%) | Urea (%) | MB-102 (%) | Urea (%) |
| 4 | 19.7 | 19.6 | 18.2 | 17.5 |
| 5 | 25.0 | 20.9 | 16.8 | 19.5 |
| 6 | 20.7 | 18.6 | 16.6 | 21.7 |
| Average | 18.7 | 19.5 | 18.9 | 19.3 |

Continuous Hemofiltration

Figure 3:
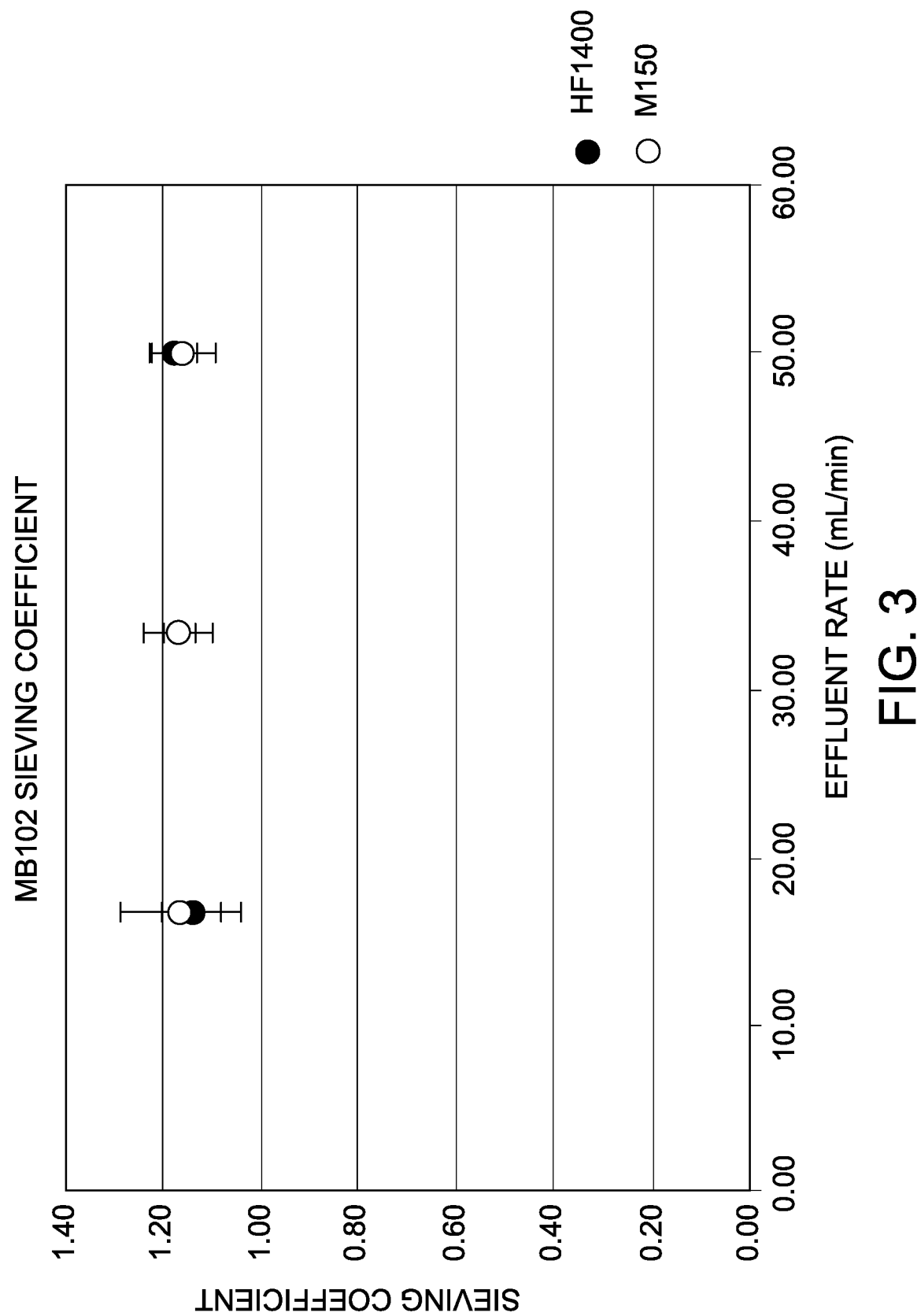
FIG. 3 is a graph of the sieving coefficients for the compound MB-102 at different effluent flow rates for the HF1400 and M150 hemodiafilters.

The mean $S_C$ values of MB-102 and urea are shown in Table 2. All MB-102 $S_c$ values are approximately 1 at three different $Q_{uf}$ with both hemodiafilters (FIG. 3). This demonstrates that MB-102 readily crosses both hemodiafilter membranes regardless of effluent flow rate. No significant difference was detected between hemodiafilter types with MB-102 and urea during the experiments. The MB-102 $CL_{TM}$ has a direct relationship ($CL_{TM}=SC \times Q_{uf}$) during CH. Since $S_C$ stays consistent as $Q_{uf}$ rises, increasing $Q_{uf}$ will increase $CL_{TM}$.

TABLE 2

Mean sieving coefficients for MB-102 and urea during CVVH experiments.

| Filter Type Ultrafiltration rate (mL/min) | HF1400 | | M150 | |
|---|---|---|---|---|
| | MB-102 | Urea | MB-102 | Urea |
| 16.7 | 1.14 ± 0.06 | 1.08 ± 0.03 | 1.17 ± 0.12 | 1.00 ± 0.05 |
| 33.3 | 1.17 ± 0.03 | 1.09 ± 0.05 | 1.17 ± 0.07 | 1.04 ± 0.10 |
| 50 | 1.18 ± 0.05 | 1.08 ± 0.07 | 1.16 ± 0.07 | 1.05 ± 0.04 |

Continuous Hemodialysis

Figure 4:
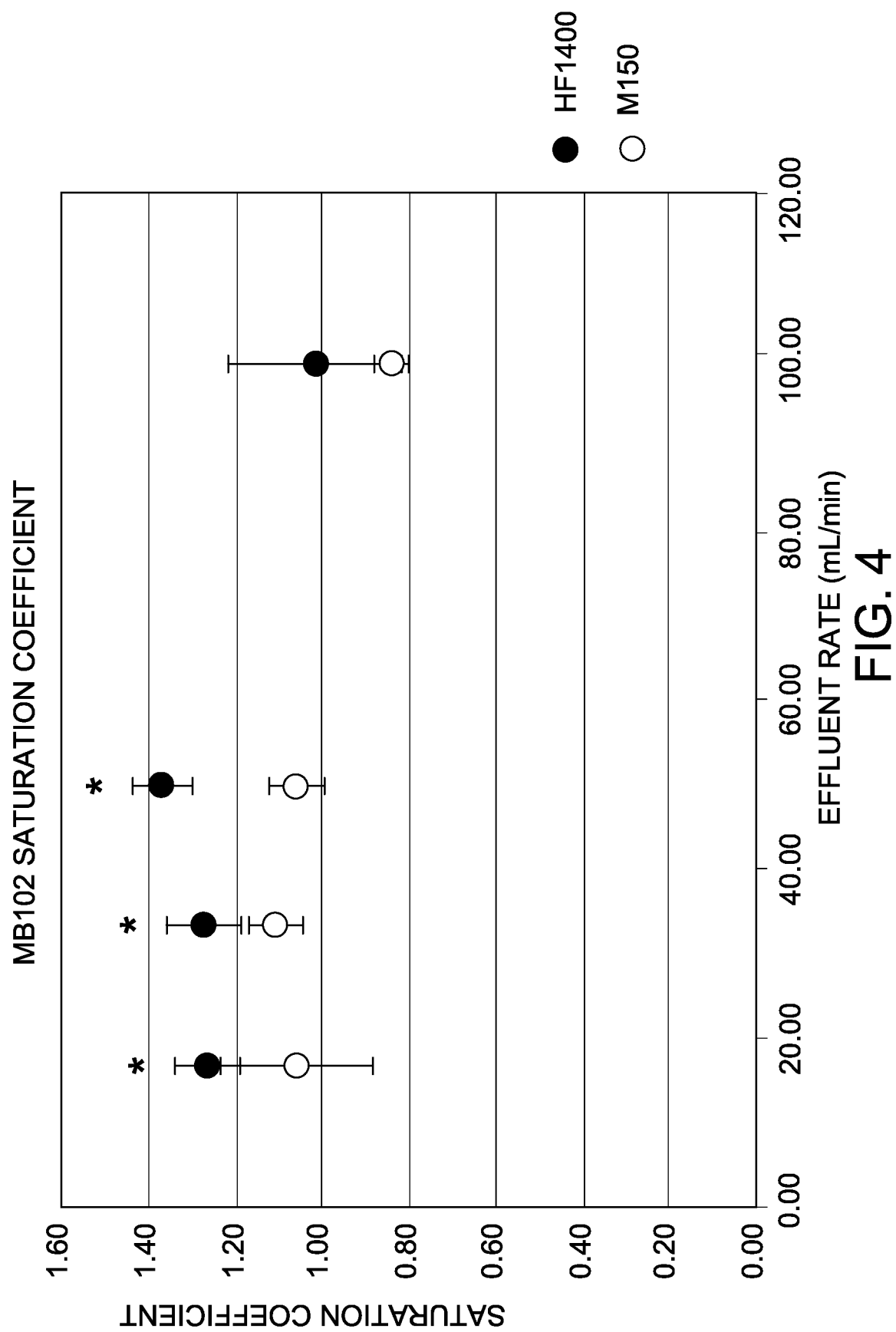
FIG. 4 is a graph of the saturation coefficients for the compound MB-102 at different effluent flow rates for the HF1400 and M150 hemodiafilters.

At low effluent flow rates (16-50 mL/min) the mean $S_A$ values of MB-102 and urea are approximately unity, meaning that the MB-102 freely passes through the membrane (Table 3). At the highest $Q_d$ (100 mL/min), effluent does not get fully saturated. Thus, $S_A$ is reduced for both hemodiafilters at $Q_d$ of 100 mL/min (FIG. 4). The HF1400 hemodiafilter had a higher $S_A$ compared to the M150 hemodiafilter at $Q_d$ of 100 mL/min, consequently resulting in a higher $CL_{TM}$.

TABLE 3

Saturation coefficients for MB-102 and urea during CVVHD experiments.

| Solute $Q_d$ | MB-102 (mean ± SD) | | | Urea (mean ± SD) | | |
|---|---|---|---|---|---|---|
| (mL/min) | HF1400 | M150 | p-value | HF1400 | M150 | p-value |
| 16.7 | 1.27 ± 0.07 | 1.06 ± 0.17 | 0.02 | 1.04 ± 0.07 | 1.08 ± 0.08 | 0.4 |
| 33.3 | 1.27 ± 0.09 | 1.11 ± 0.06 | 3.5e−3 | 1.19 ± 0.09 | 1.16 ± 0.04 | 0.5 |
| 50 | 1.37 ± 0.07 | 1.60 ± 0.06 | 9.5e−6 | 1.17 ± 0.11 | 1.15 ± 0.15 | 0.8 |
| 100 | 1.02 ± 0.20 | 0.84 ± 0.04 | 0.06 | 1.17 ± 0.19 | 1.35 ± 0.20 | 0.1 |

This in vitro study demonstrates that MB-102 does not bind to CRRT tubing or to either hemodiafilter, but rather is readily cleared by different CRRT modalities (CVVH and CVVHD). MB-102 $S_C$ and $S_A$ are approximately 1, similar to urea. This suggests that pharmacokinetic parameters of MB-102 (0% protein binding and small molecular weight) allow free passage across the hemodiafilter membrane. With CVVHD, the less permeable membrane (M150) begins to show a $S_A$ reduction at high $Q_d$ (100 mL/min; close to what is observed with sustained low efficiency dialysis).

In Vivo Clearance of MB-102 By CRRT in a Porcine Model

Animal Preparation

Swine (3 male and 3 female, for both CVVH and CVVHD modalities) weighing 35-40 kg were used. In this model, a total functional nephrectomy was achieved by ligation of all renal arteries. Animals were inspected by professional veterinary staff within 48 hours of arrival. Any underlying infections or parasitism was treated based on veterinary recommendations.

Prior to study, the animals were fasted overnight (with water ad libitum) to reduce the risk of aspiration. On the morning of the study, animals were sedated with an intramuscular injection of Telazol/Xylazine (or a Ketamine/xylazine combination) at recommended doses and transported to the operating theatre. Pigs were then anesthetized via inhalation of 5% isoflurane in oxygen via mask. A catheter was placed in the marginal ear vein to provide immediate venous access for further medications and IV fluids.

Pigs were orotracheally intubated and the isoflurane concentration reduced to 1%-3% to maintain anesthesia for the duration of the experiment. Pigs were mechanically ventilated using a tidal volume of 10 mL/kg and respiratory rate adjusted to keep a P(CO2) of 40±2 mmHg. A three lead electrocardiogram was used to monitor heart rate and rhythm. Core body temperature was measured with a rectal thermistor probe and maintained at 37-39° C. with the use of a circulating water blanket.

Hair was removed from the ventral neck, abdominal and/or the femoral regions, and these sites were prepared for aseptic surgery. Lidocaine was injected at incision site(s). When a surgical plane of anesthesia was reached, the right carotid artery was approached via cut down incision and cannulated for continuous blood pressure monitoring. This facilitated withdrawal of blood samples for the study and for the determination of respiratory gases, acid-base status and glucose concentration. A catheter was placed in the right jugular/femoral vein to infuse medications or replacement fluids and an 11 Fr hemodialysis catheter was placed into the left jugular vein for both CVVH and CVVHD procedures.

The abdomen was then opened via a midline laparotomy. The renal hilum was identified, and ties were placed around the renal artery or arteries: for partial or total ligation as dictated by study requirements (full-function nephrectomy via total ligation of all renal arteries, and full-function nephrectomy of one kidney and partial ligation of the second kidney). Perivascular flow probes were placed around the proximal renal artery of the kidneys in situ, as required. The areas were observed for any signs of bleeding and flow probe stability was verified. A purse-sting suture was placed in the urinary bladder and a small cystotomy incision was performed to advance a Foley catheter for urine collection and quantification, as required.

Due to the length of time of study, the abdomen was closed in 2-3 layers with appropriate suture material to prevent desiccation of tissues. Suture patterns allowed for external extension of tubing and flow probe lines for equipment attachment as required. Following complete instrumentation, the pig was stabilized. Vital signs were monitored continuously and, once stable, either the CVVH and CVVHD experiment was initiated.

MB-102 Dosing and Protocol

Figure 7:
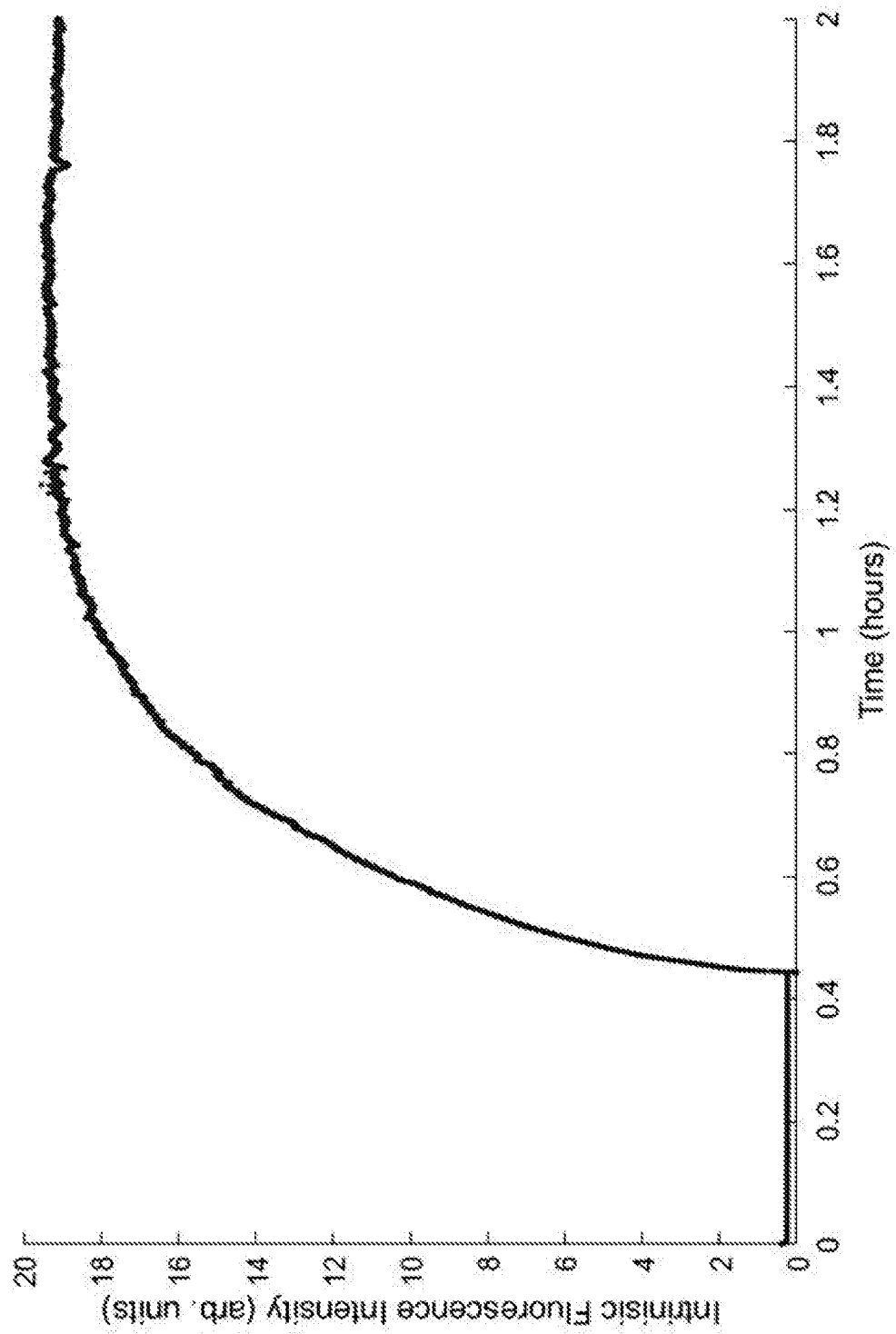
FIG. 7 is a graph of the increase in detected fluorescence in a porcine model having a bilateral nephrectomy at the beginning of CVVH.
Figure 13:
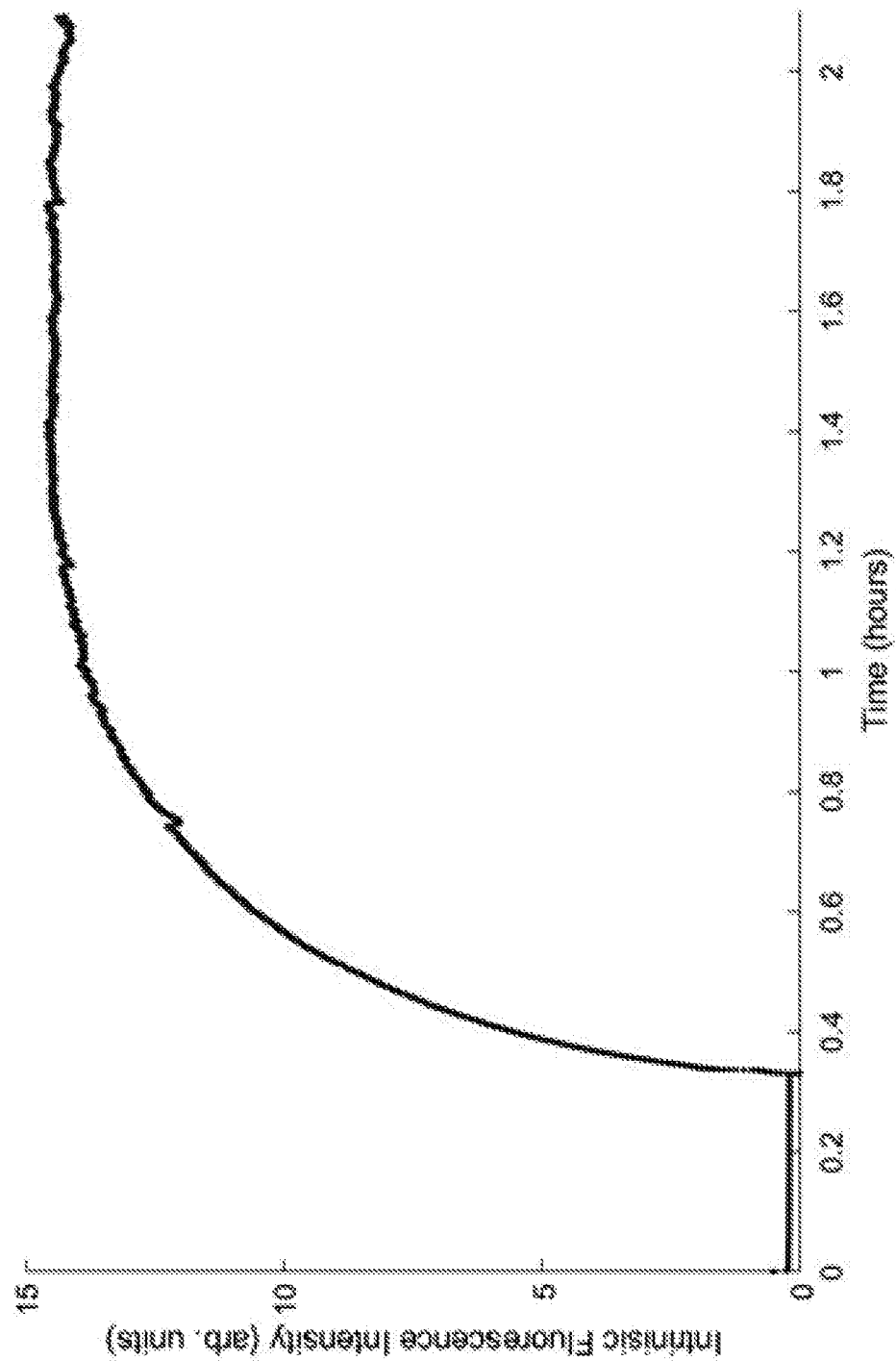
FIG. 13 is a graph of the increase in detected fluorescence in a porcine model having a bilateral nephrectomy at the beginning of CVVHD.

After taking a pre-MB-102 blood sample (baseline), a dose of 6 mg/kg of MB-102 was injected as a single bolus, followed by a 90 minute period of equilibration, to allow for MB-102 systemic redistribution (see FIGS. 7 and 13 for equilibration of fluorescent signal detected by the renal monitoring assembly). Thirty minutes after the MB-102 injection, Meropenum was infused for 30 minutes, which reached a peak concentration in blood ~1 hr after the start of the infusion. After drug equilibration, CRRT was initiated (either CVVH or CVVHD) at a blood flow rate (BFR) of 100 mL/min with corresponding 20 mL/kg/hr effluent rate during a time-course of 90 minutes (with collections at 0, 30, 60, 90 minutes). The effluent rate was increased to 35 mL/kg/hr during a time-course of 45 minutes (with collections at 15, 30, 45 minutes). Samples collected during these periods, along with the baseline (BSL) sample taken before the MB-102 dose, were assayed, and measured values were used in calculations to compare clearance rates with real-time MB-102 clearance measurements. In addition to the BSL sample, seven sample time points were collected at three circuit sites (pre-hemodiafilter [pre HF], post-hemodiafilter [post HF] and effluent [UF/SD]) for both the low and high flow rates. CRRT flow rates were adjusted in steps in order to transition to high BFR (200 mL/min) over a 30 minute transition period. A similar sample collection time-course was initiated at the high flow rate for both the low and high effluent flow rate data sets (seven sample time points at three circuit sites), allowing for similar comparisons of real-time and calculated clearance rates.

Heparin was administered systemically (initial injection of 3-5 mL Heparin (1,000 U/mL), followed by infusion of 1-2 mL/hr) and Duosol (35 mEq bicarbonate, 4 mEq K+, 3 mEq Ca++ and 1 g/L glucose) were used as the replacement fluid (RF).

Figure 18:
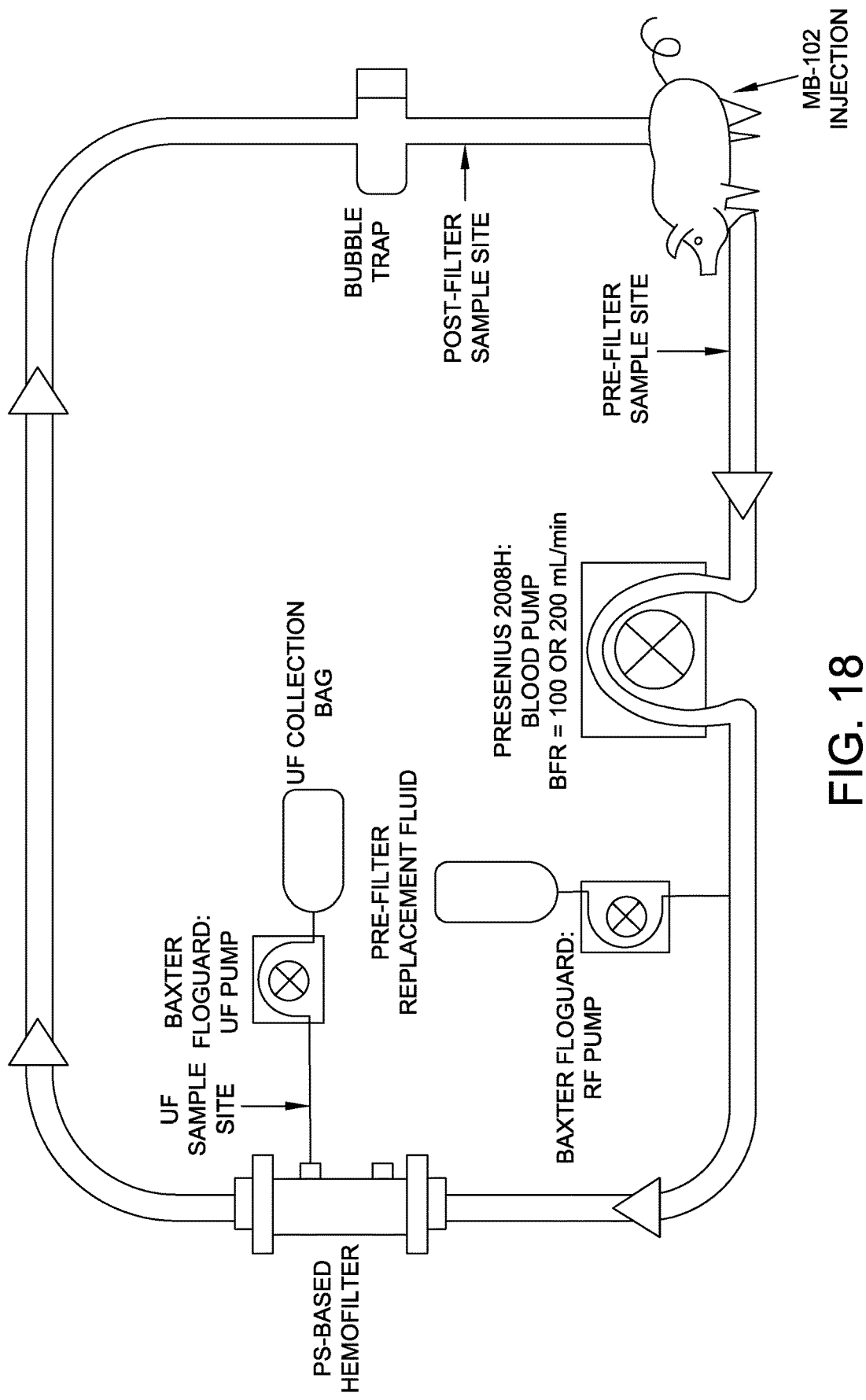
FIG. 18 is a schematic representation of the in vivo CVVH system used for the porcine model.
Figure 19:
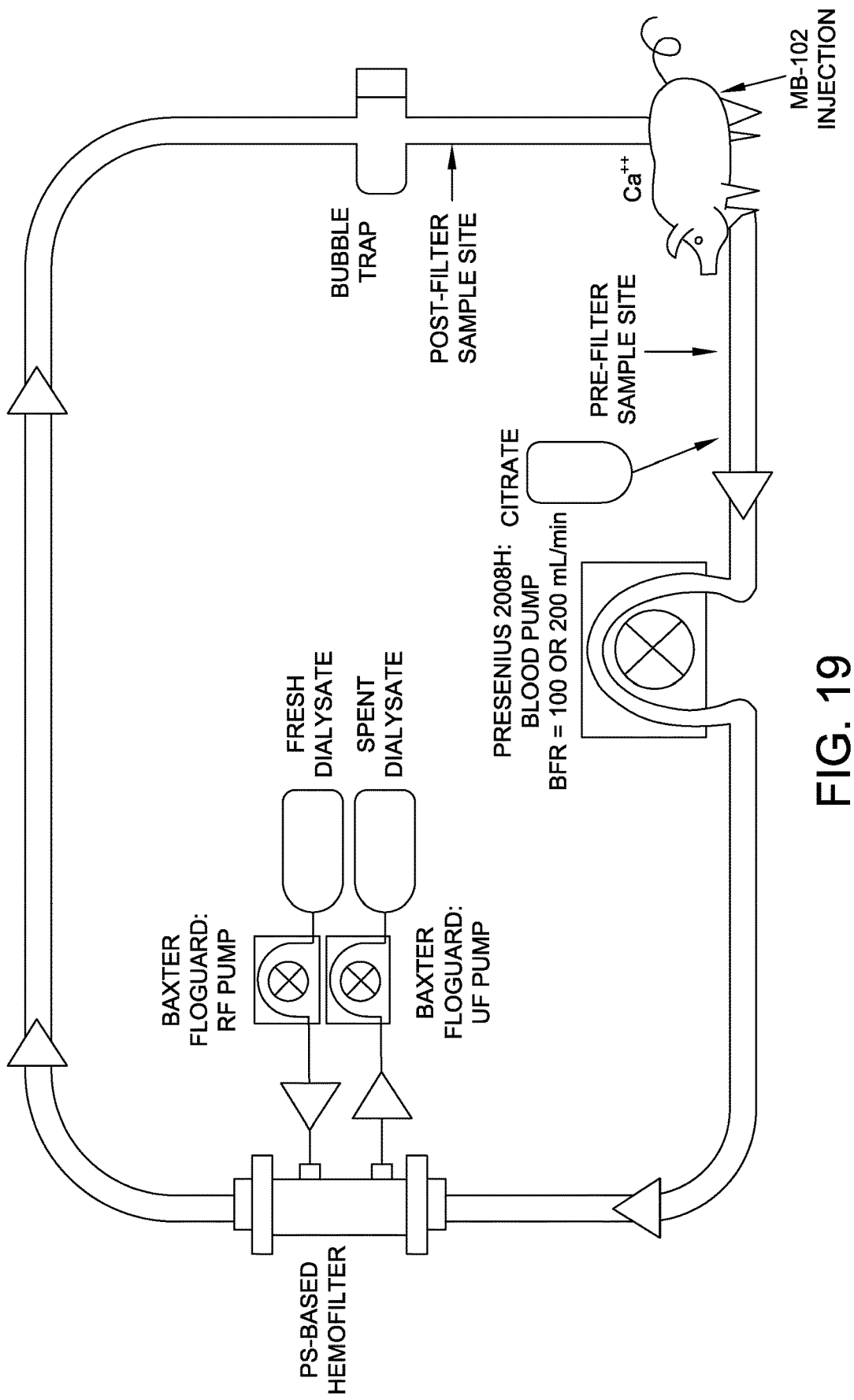
FIG. 19 is a schematic representation of the in vivo CVVHD system used for the porcine model.

Shown in FIGS. 18 and 19 are schematic representations for the CVVH (FIG. 18) and CVVHD (FIG. 19) circuits used herein.

CVVH Results

Figure 8:
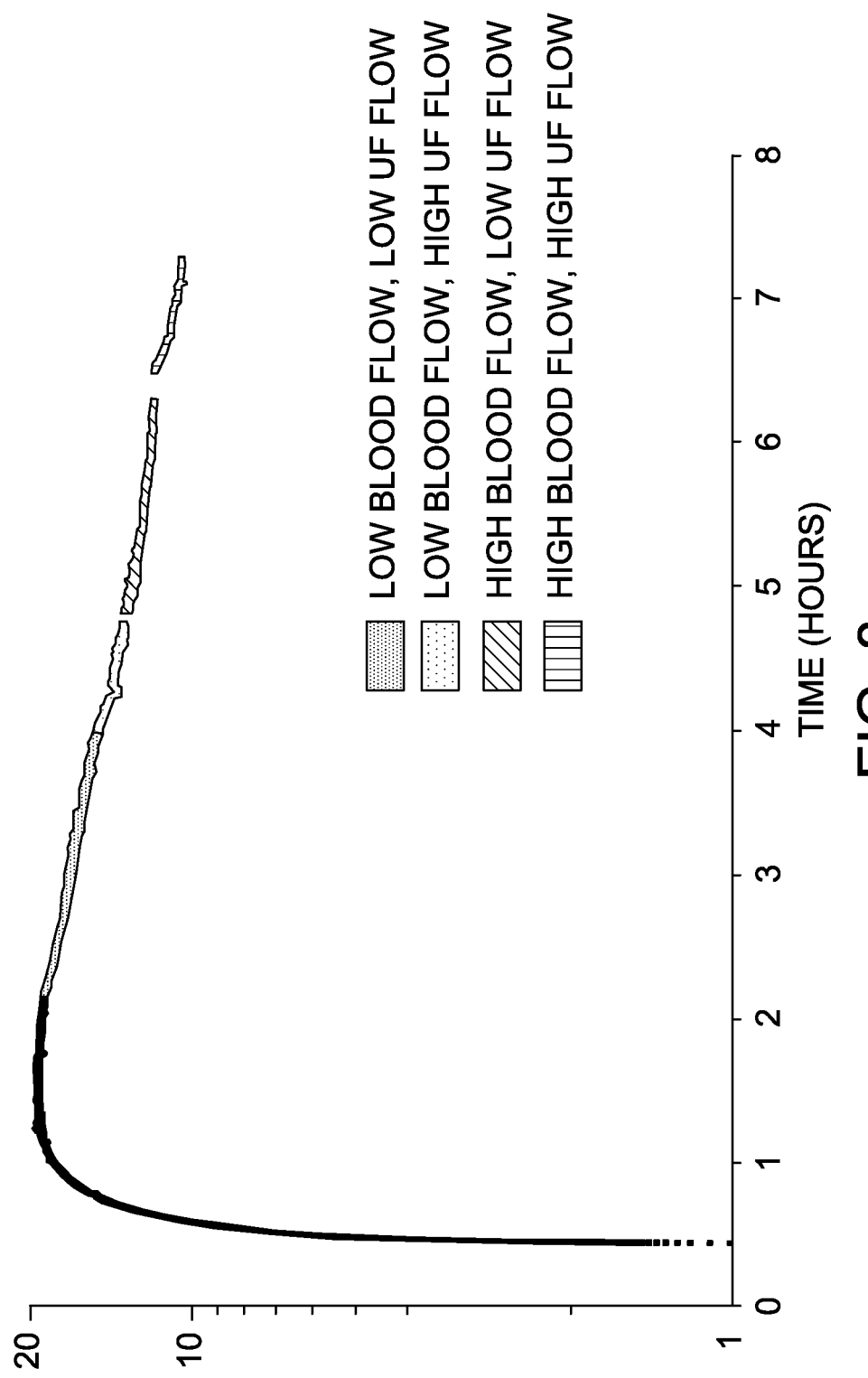
FIG. 8 is a graph illustrating the decrease in detected fluorescence (linear scale) in a porcine model during CVVH as a function of time.
Figure 9:
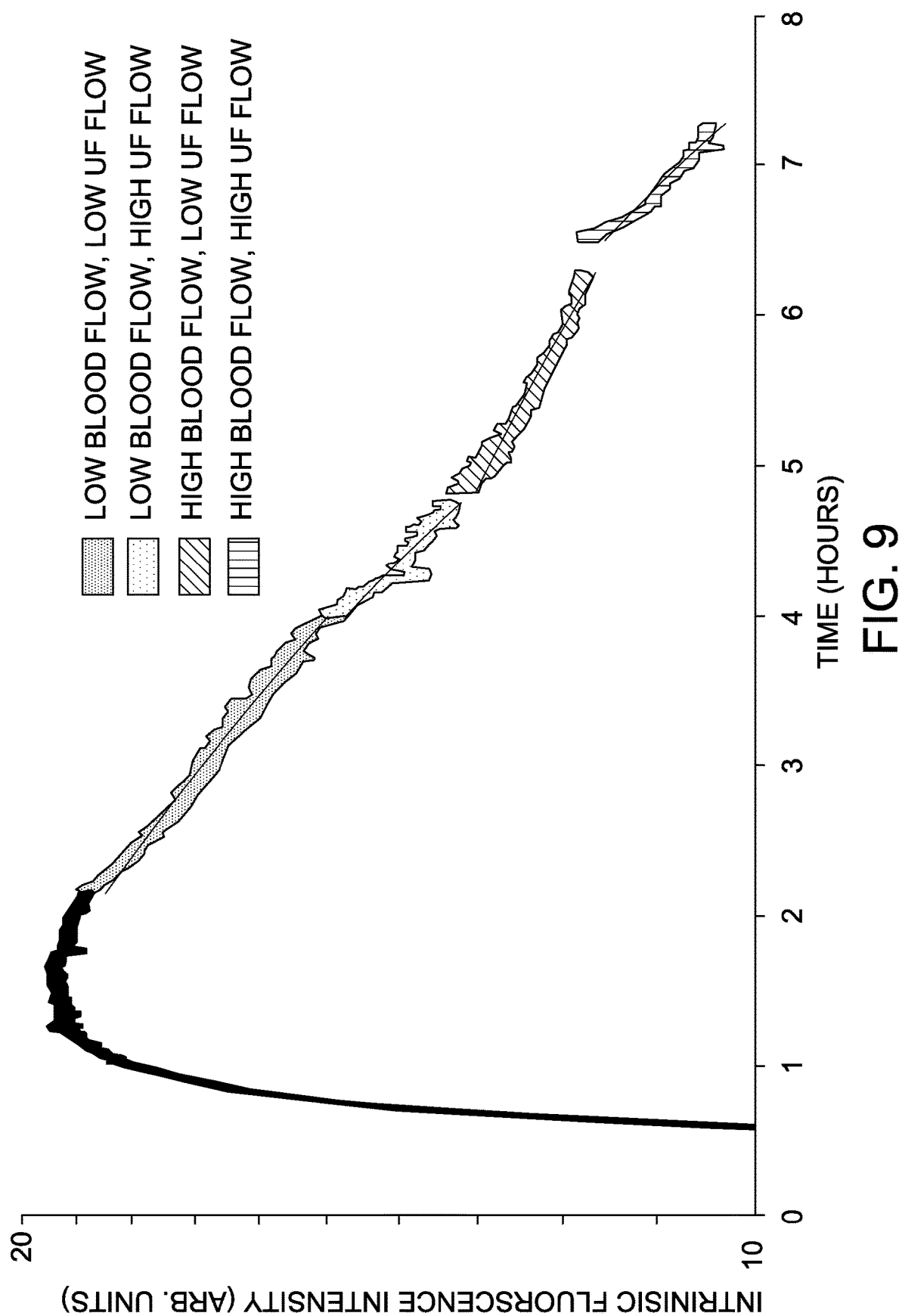
FIG. 9 is a graph illustrating the decrease in detected fluorescence (logarithmic scale) in a porcine model during CVVH as a function of time.
Figure 20:
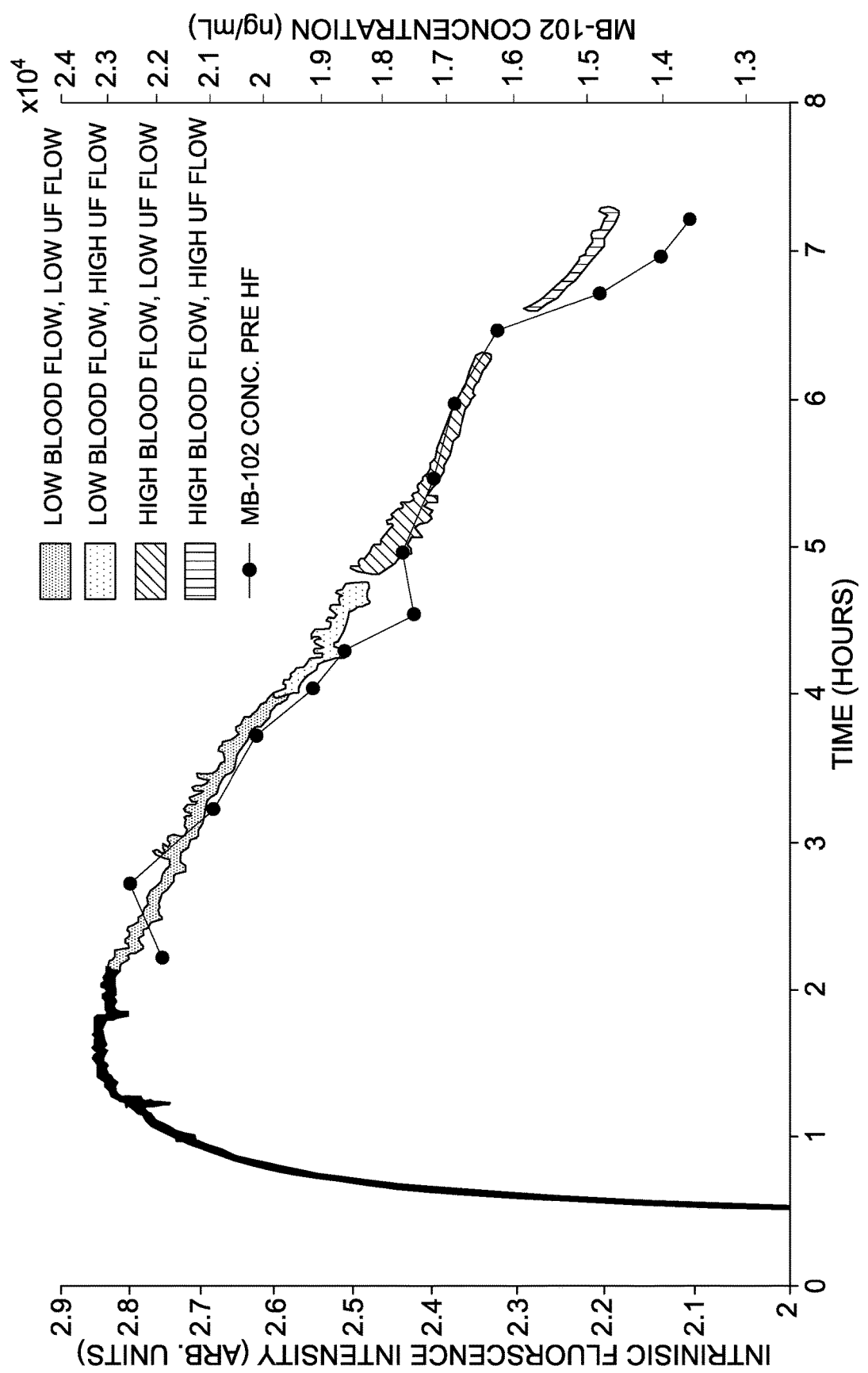
FIG. 20 is a graph of the plasma concentration of MB-102 as a function of time during the CVVH experiment overlaid on detected fluorescence.

As shown in Tables 4 and 5, and illustrated in FIGS. 7, 8, 9, 10, 11, and 12, MB-102 is cleared from the bloodstream of a pig having a bilateral nephrectomy undergoing CVVH with a renal decay time constant (RDTC) of from 6.90 to 13.11. The RDTC is a function of flow rate of both the blood and effluent in the CVVH apparatus. Before initiating CVVH, MB-102 builds up to a steady state concentration in the bloodstream as shown in FIG. 7. During the procedure, both the blood and effluent flow rates were varied as illustrated by the four different regions in the graphs (FIGS. 8 and 9). As illustrated, CVVH clears MB-102 from the bloodstream at a rate based on the blood and effluent flow rates. Higher flow rates of the effluent resulted in a lower RDTC which results in a higher rate of clearance of the MB-102. As seen in FIG. 20, the concentration of MB-102 in the blood stream correlates well with the detected fluorescence at all blood and effluent flow rates.

Placement of the renal monitoring assembly on either the sternum (FIGS. 10 and 11 and Table 4) or the chest (FIG. 12 and Table 5) of the patient gave virtually identical results (within the experimental error). FIGS. 11 and 12 illustrate expansions of the time curve during the CVVH procedure and the linear best fit calculations. Semi-log fits were obtained by taking the log of the intensity values, plotting the data as a function of time and fitting the line using MATLAB 'polyfit' function.

TABLE 4

Figure 10:
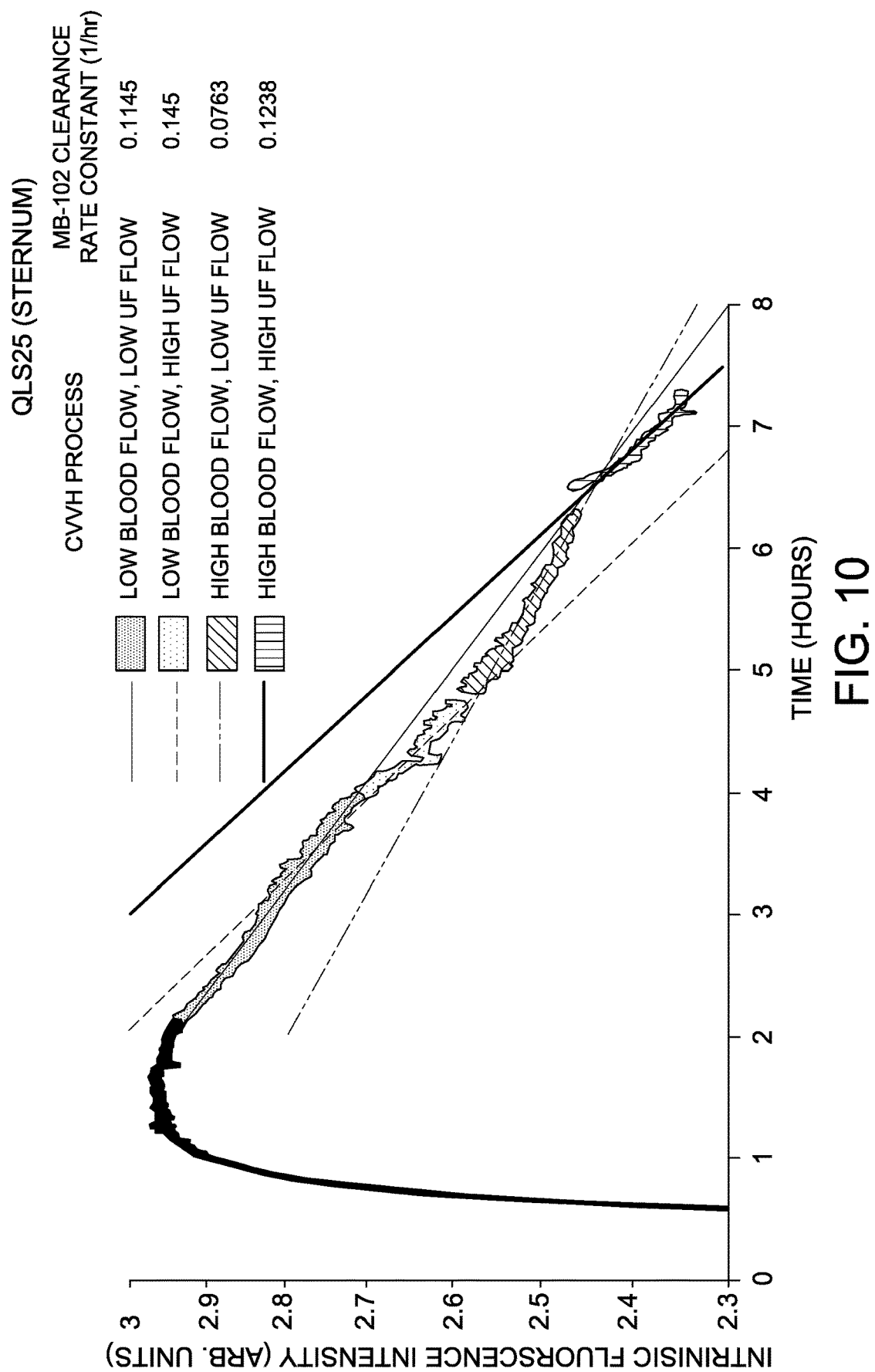
FIG. 10 is a graph illustrating the calculations to determine the MB-102 clearance rate at different flow rates during CVVH as measured with the renal monitoring assembly located on the sternum of a pig.
Figure 11:
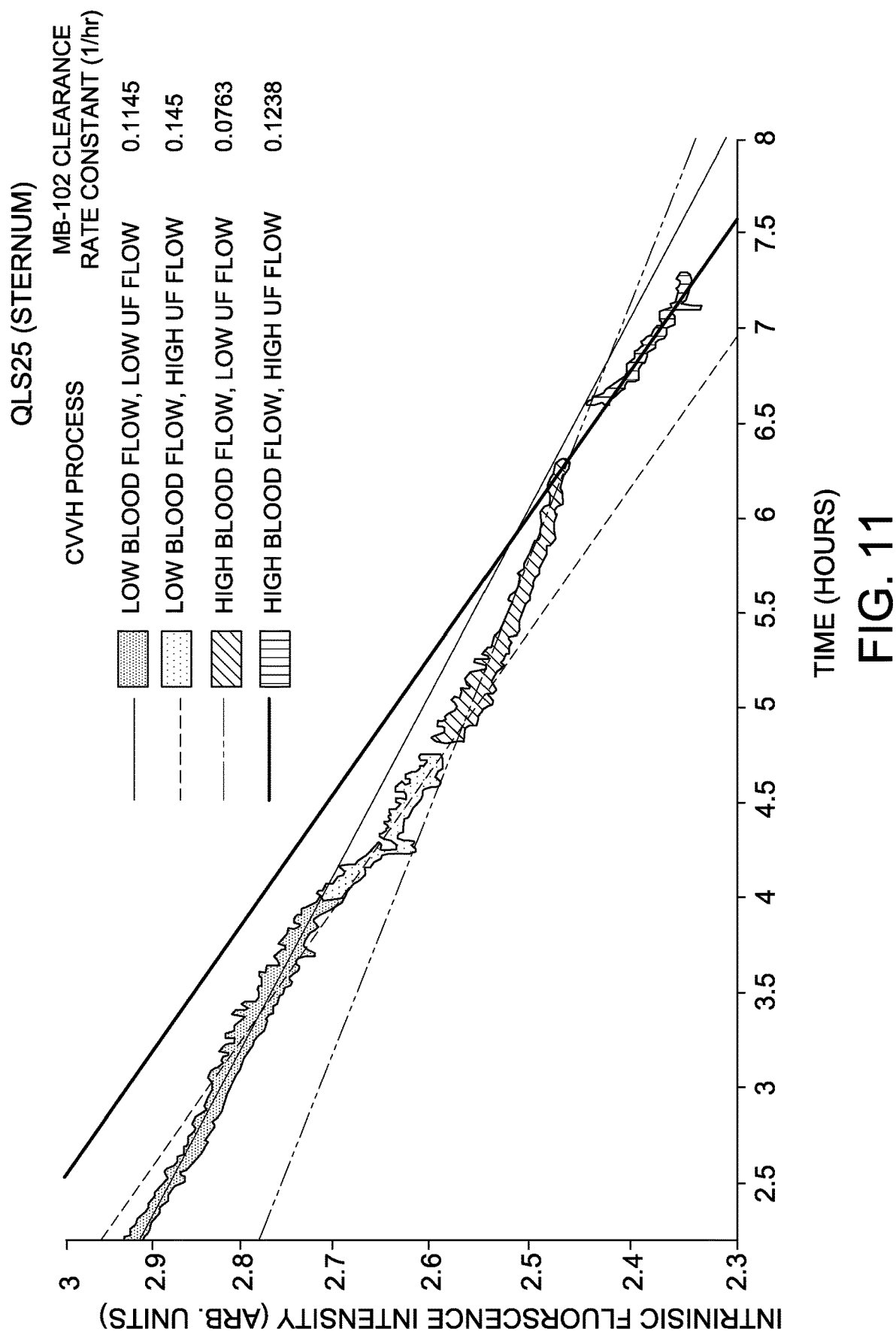
FIG. 11 is a graph illustrating the calculations to determine the MB-102 clearance rate at different flow rates during CVVH as measure with the renal monitoring assembly located on the sternum of the pig.
Figure 12:
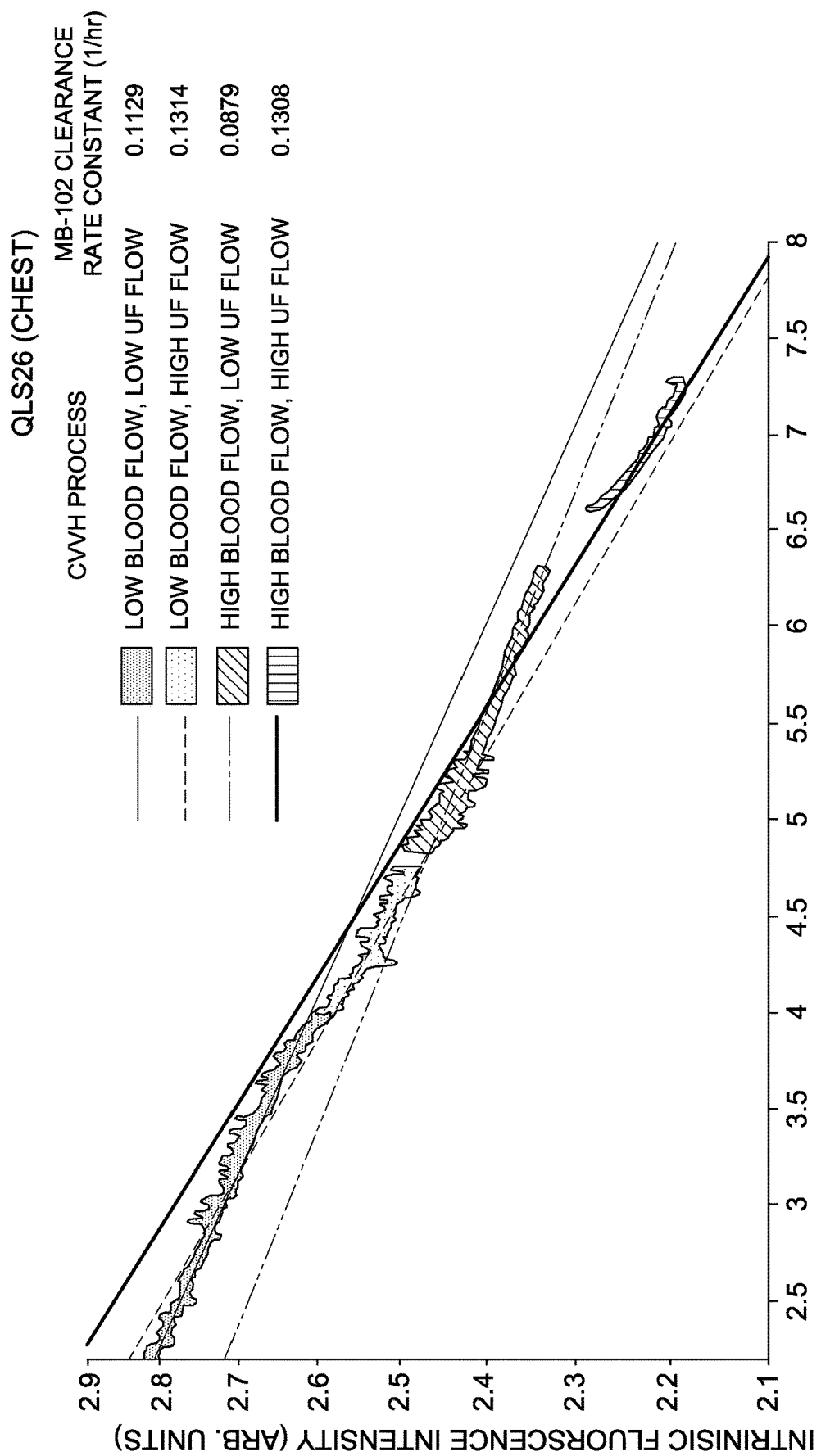
FIG. 12 is a graph illustrating the calculations to determine the MB-102 clearance rate at different flow rates during CVVH as measured with the renal monitoring assembly located on the chest of a pig.

RDTC and GFR for QLS25 during CVVH with the renal monitoring assembly on patient sternum (Figure 10 and 11).

| Blood Flow Rate* | Effluent Flow Rate* | MB-102 Clearance Rate Constant (1/hr) | RDTC (hrs) |
| --- | --- | --- | --- |
| 100 | 20 | 0.1145 | 8.73 |
| 200 | 35 | 0.145 | 6.90 |
| 100 | 20 | 0.0763 | 13.11 |
| 200 | 35 | 0.1238 | 8.08 |

*All flow rates are in mL/min.

TABLE 5

RDTC and GFR for QLS26 during CVVH with the renal monitoring assembly on patient chest (Figure 12).

| Blood Flow Rate* | Effluent Flow Rate* | MB-102 Clearance Rate Constant (1/hr) | RDTC (hrs) |
| --- | --- | --- | --- |
| 100 | 20 | 0.1129 | 8.86 |
| 200 | 35 | 0.1314 | 7.61 |
| 100 | 20 | 0.0879 | 11.38 |
| 200 | 35 | 0.1308 | 7.64 |

*All flow rates are in mL/min.

CVVHD Results

Figure 14:
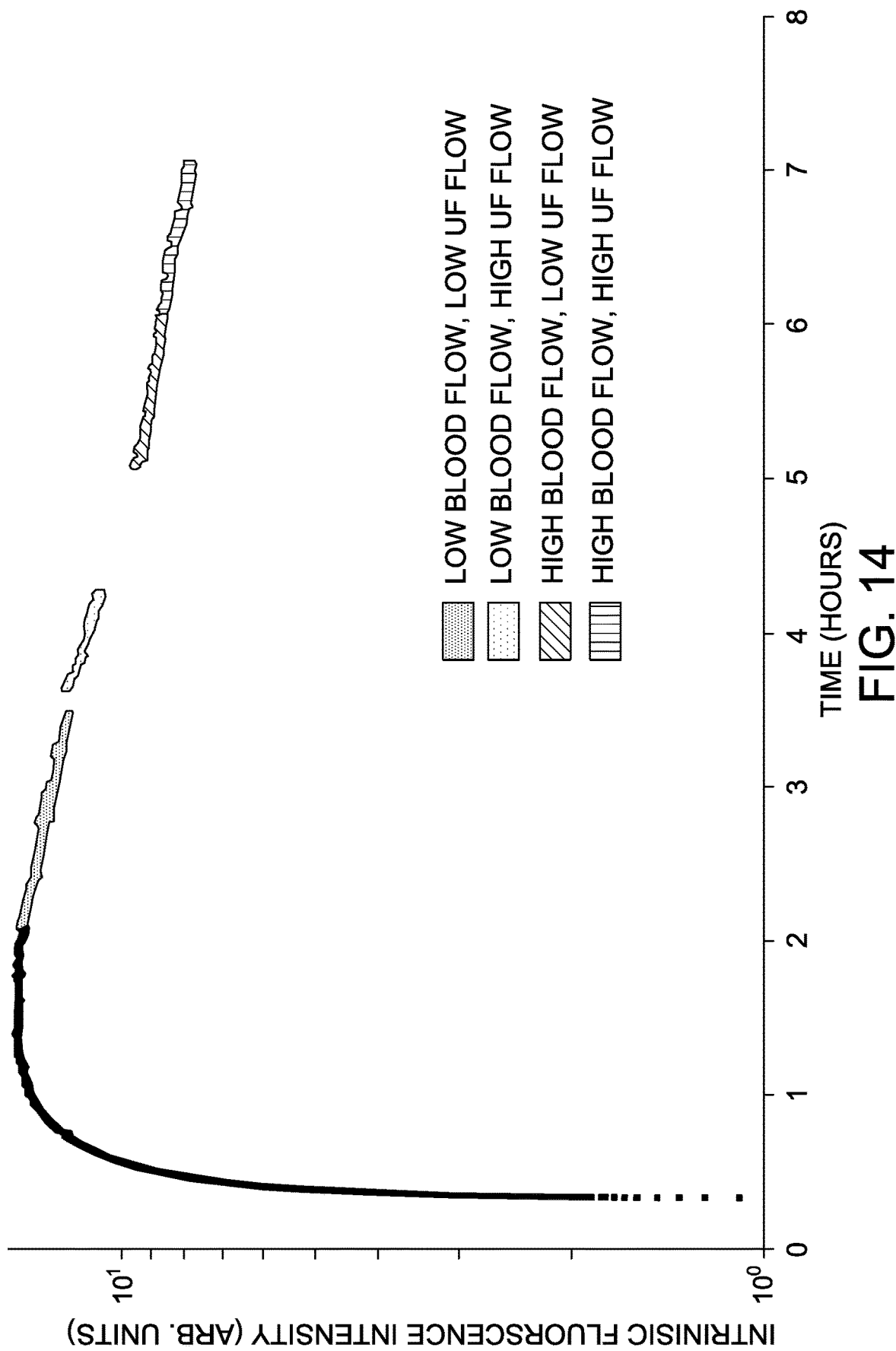
FIG. 14 is a graph illustrating the decrease in detected fluorescence (linear scale) in a porcine model during CVVHD as a function of time.
Figure 15:
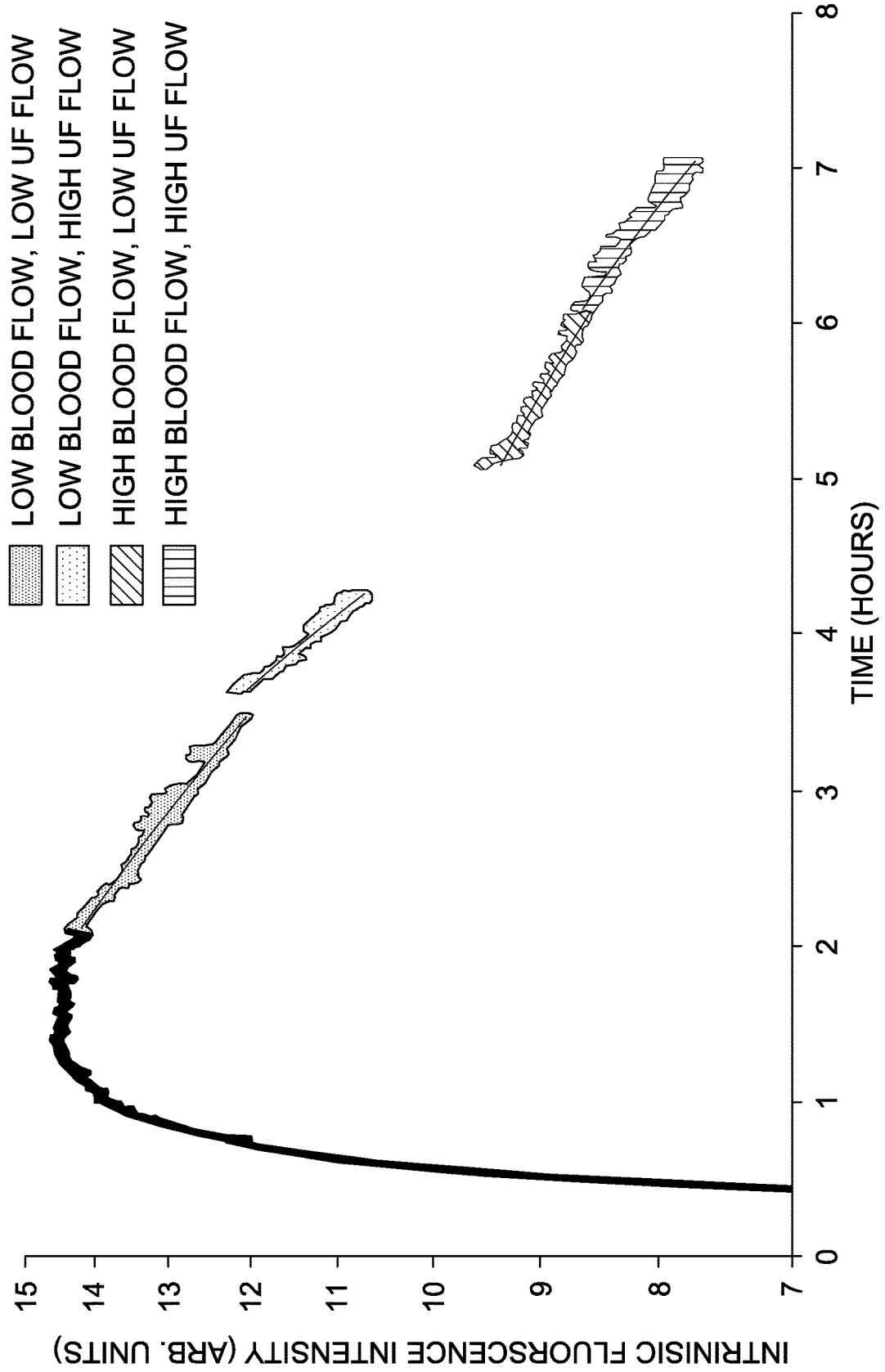
FIG. 15 is a graph illustrating the decrease in detected fluorescence (logarithmic scale) during CVVHD as a function of time.
Figure 21:
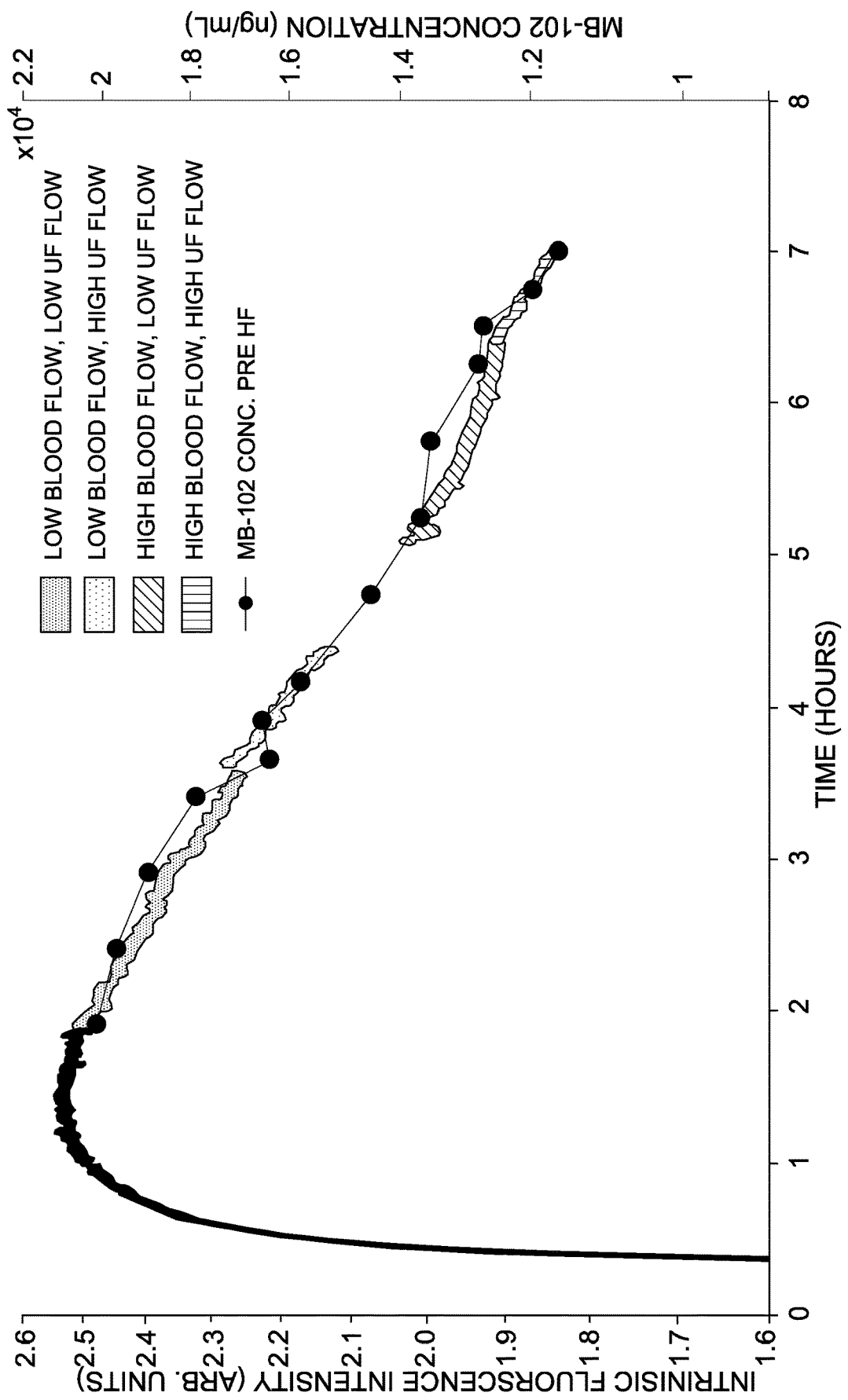
FIG. 21 is a graph of the plasma concentration of MB-102 as a function of time during the CVVHD experiment overlaid on detected fluorescence.

As shown in Tables 6 and 7 and FIGS. 13, 14, 15, 16 and 17, MB-102 is cleared from the bloodstream of a pig having a bilateral nephrectomy undergoing CVVHD with a RDTC of from 7.61 to 11.38. Before initiating CVVHD, MB-102 builds up to a steady state concentration as illustrated in FIG. 13. During the procedure, both the blood and effluent flow rates were varied as illustrated by the four different regions in the graphs (FIGS. 14 and 15). Once initiated, CVVH clears MB-102 from the bloodstream at a rated based on the blood and effluent flow rates. Higher flow rates of the effluent resulted in a higher rate of clearance which results in a lower RDTC. This in turn results in a higher rate of clearance of MB-102. As seen in FIG. 21, the concentration of MB-102 in the blood stream correlates well with the detected fluorescence at all blood and spent effluent flow rates.

Figure 16:
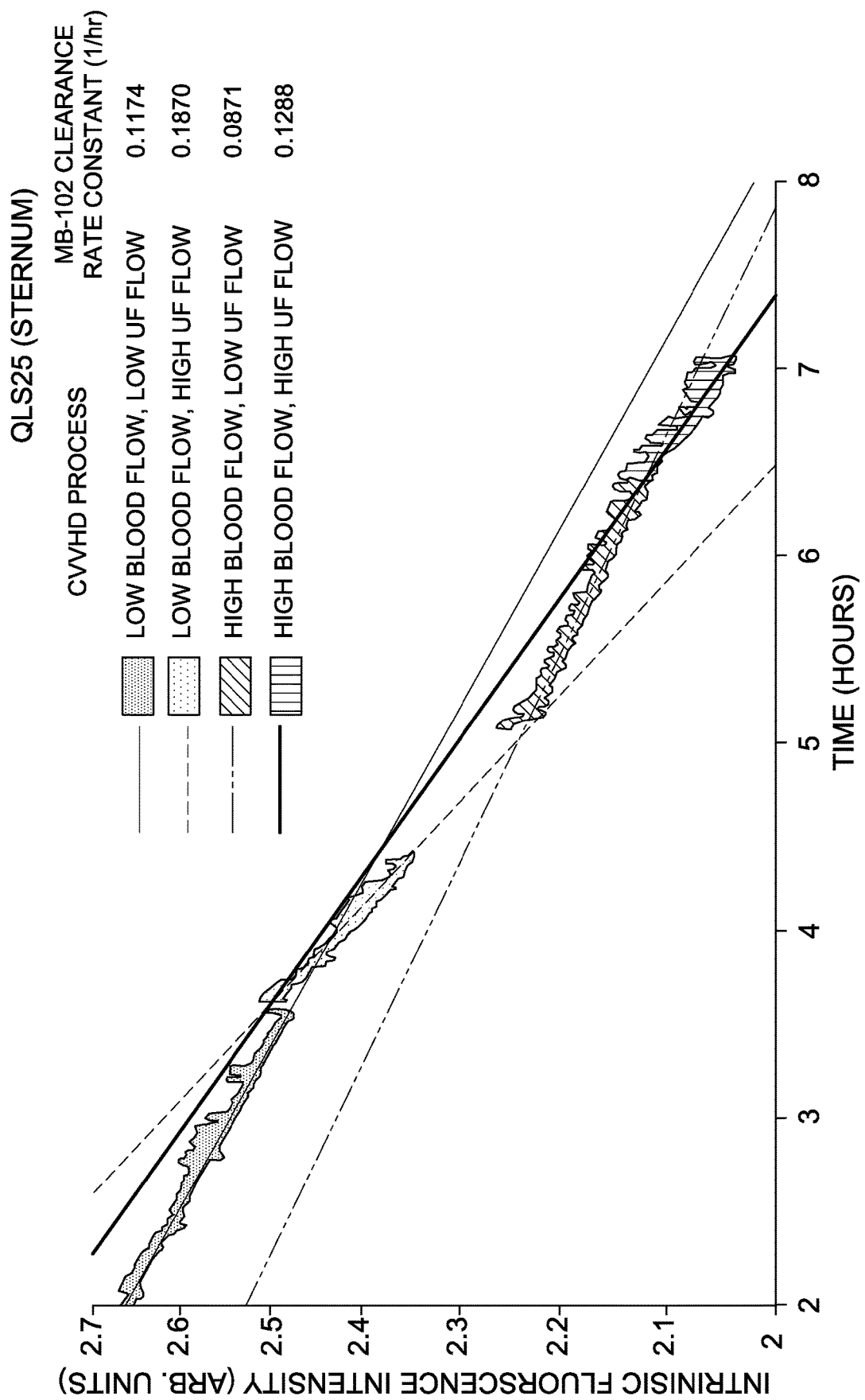
FIG. 16 is a graph illustrating the calculations to determine the MB-102 clearance rate at different flow rates during CVVHD as measured with the renal monitoring assembly located on the sternum of a pig.
Figure 17:
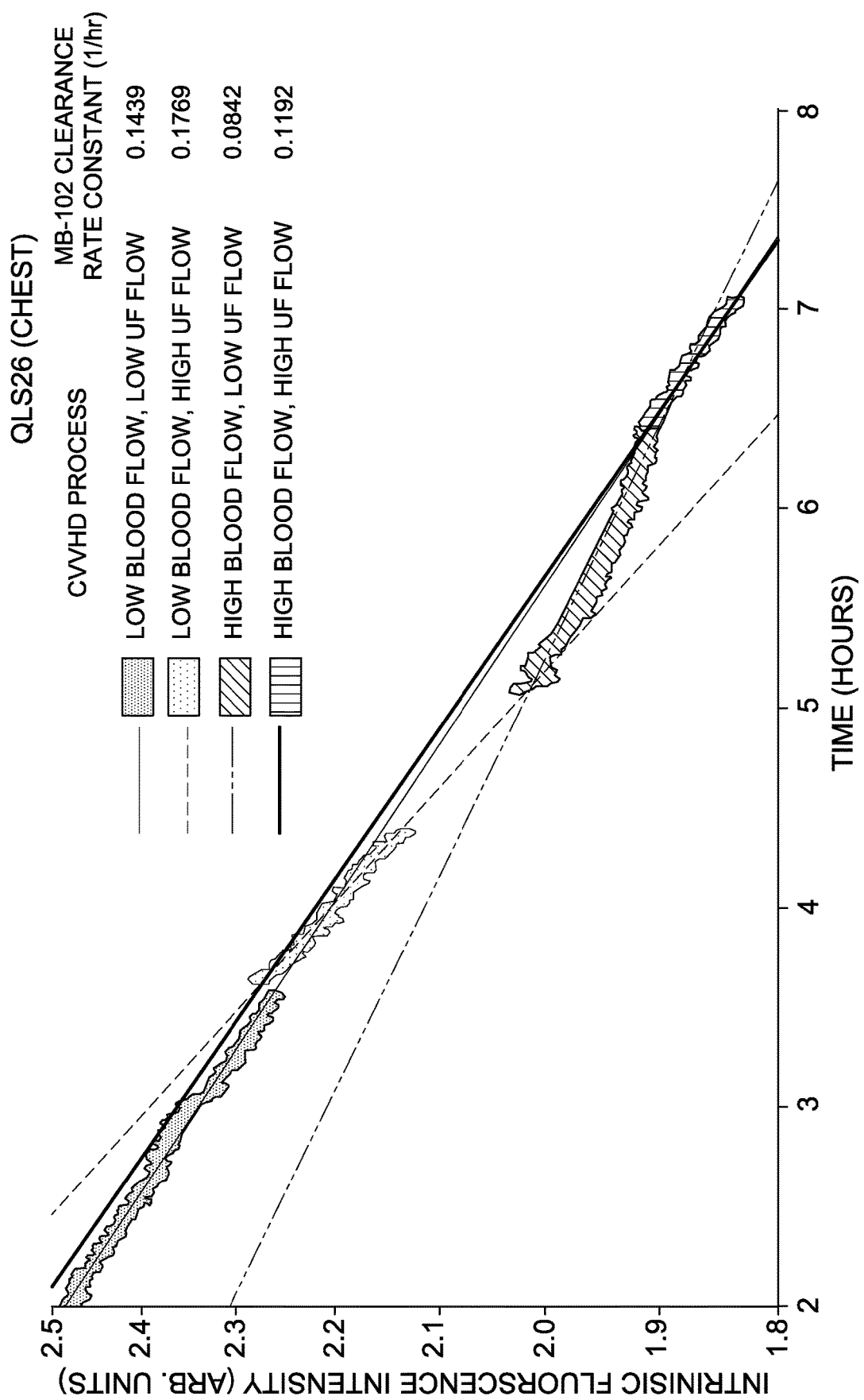
FIG. 17 is a graph illustrating the calculations to determine the MB-102 clearance rate at different flow rates during CVVHD as measured with the renal monitoring assembly located on the chest of a pig.

Placement of the renal monitoring assembly on either the sternum (FIG. 16 and Table 6) or the chest (FIG. 17 and Table 7) gave virtually identical results (within the experimental error). FIGS. 16 and 17 illustrate expansions of the time curve during the CVVHD and the linear best fit calculations. In the same manner as for the CVVH experiments, semi-log fits were obtained by taking the log of the intensity values, plotting the data as a function of time and fitting the line using MATLAB 'polyfit' function.

TABLE 6

RDTC and GFR for QLS25 during CVVHD with the renal monitoring assembly placed on sternum (Figure 16).

| Blood Flow Rate* | Effluent Flow Rate* | MB-102 Clearance Rate Constant (1/hr) | RDTC (hrs) |
| --- | --- | --- | --- |
| 100 | 20 | 0.1174 | 8.52 |
| 200 | 35 | 0.1870 | 5.35 |
| 100 | 20 | 0.0871 | 11.48 |
| 200 | 35 | 0.1288 | 7.76 |

*All flow rates are in mL/min.

TABLE 7

RDTC and GFR for QLS26 during CVVHD with the renal monitoring assembly placed on chest (Figure 17).

| Blood Flow Rate* | Effluent Flow Rate* | MB-102 Clearance Rate Constant (1/hr) | RDTC (hrs) |
| --- | --- | --- | --- |
| 100 | 20 | 0.1439 | 6.94 |
| 200 | 35 | 0.1769 | 5.65 |
| 100 | 20 | 0.842 | 11.87 |
| 200 | 35 | 0.1192 | 8.39 |

*All flow rates are in mL/min.

In Vivo Clearance of Meropenem by CRRT

The same in vivo experimental setup used to monitor MB-102 clearance in the porcine model, supra, was used to determine the clearance rate for meropenem in vivo (see FIGS. 18 and 19). The same samples that were analyzed for MB-102 concentration were also analyzed for meropenem concentration.

Figure 22:
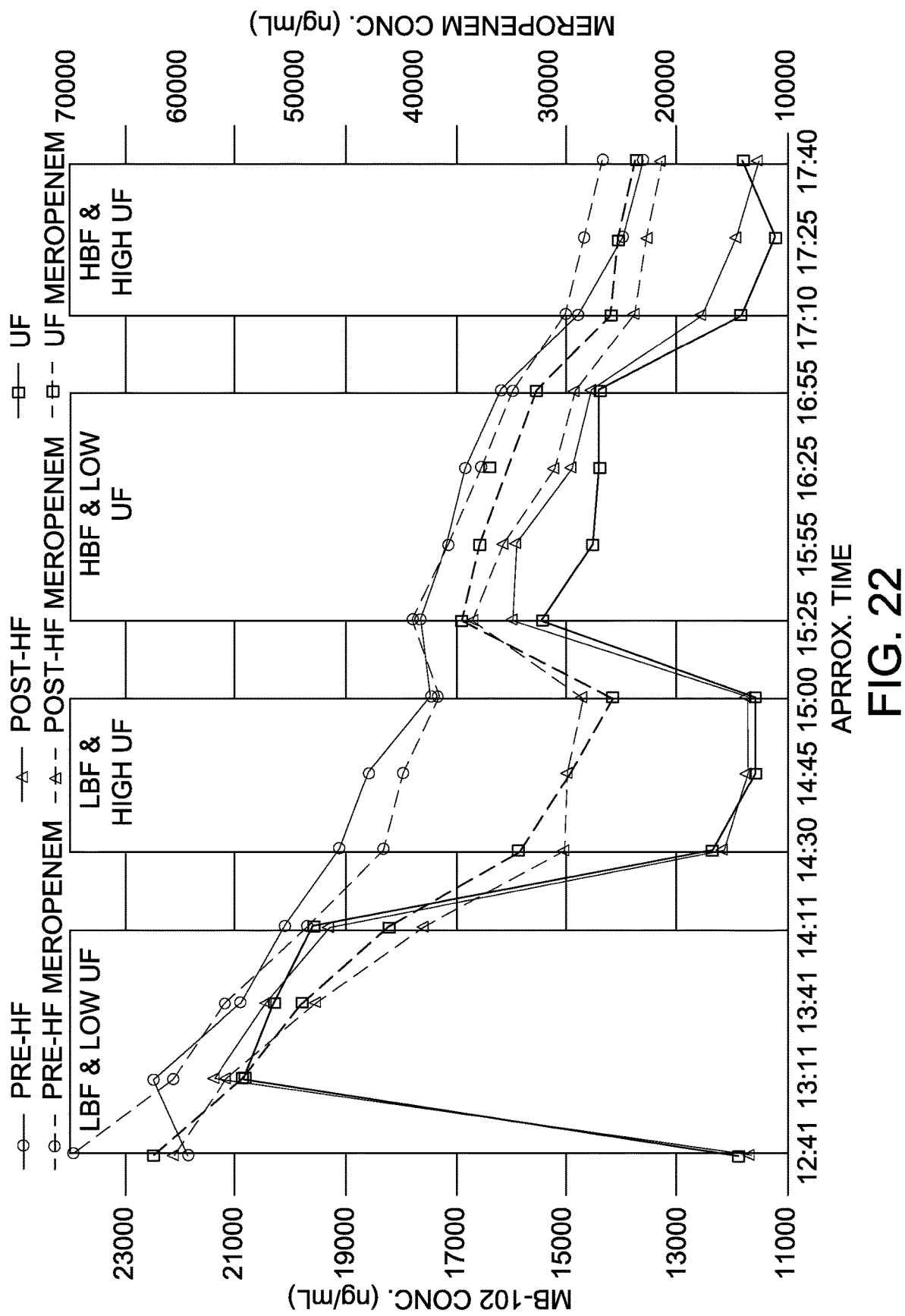
FIG. 22 is a graph of meropenem concentration as a function of time and flow rate during a CVVH experiment with a porcine model.
Figure 23:
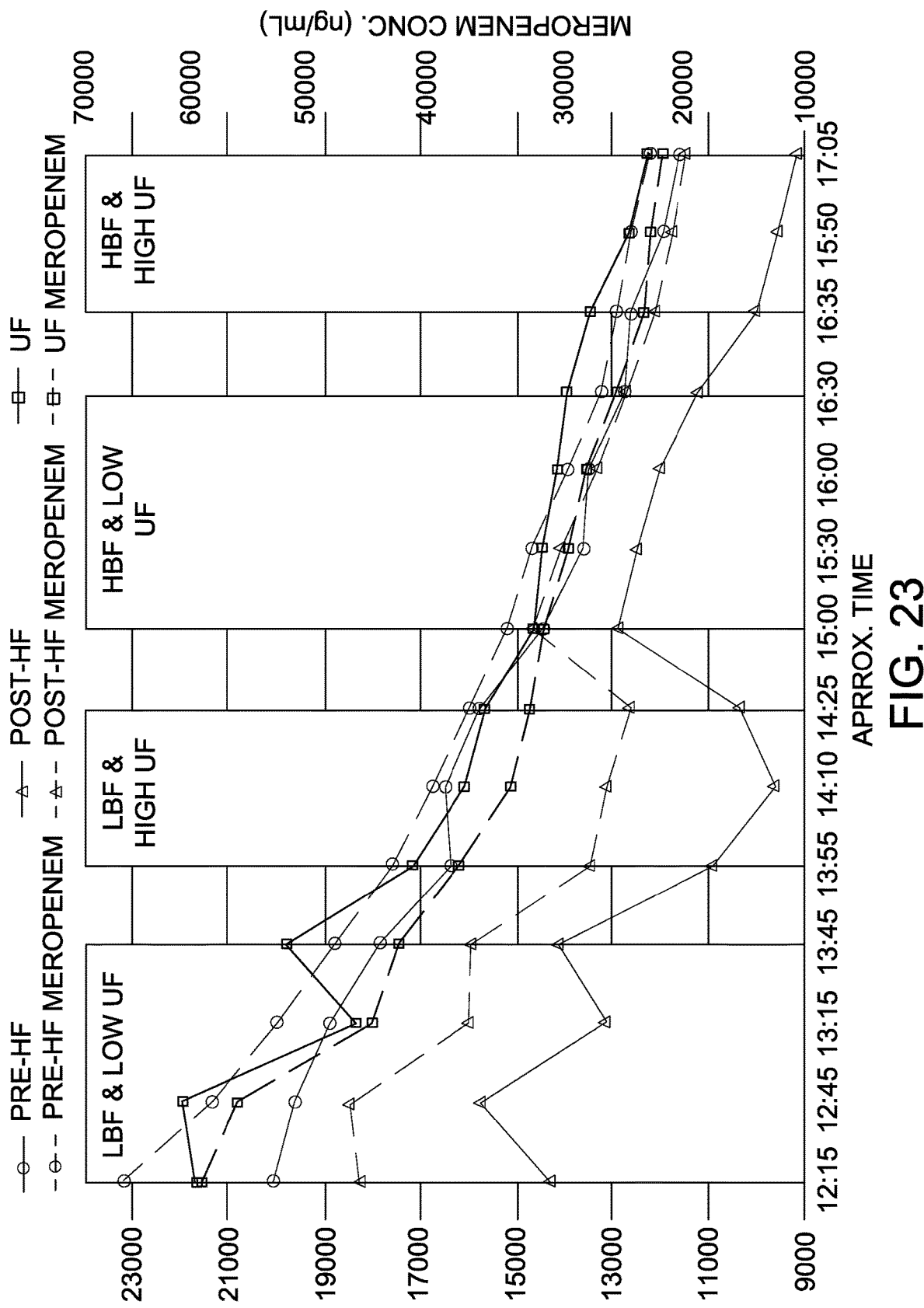
FIG. 23 is a graph of meropenem concentration as a function of time and flow rate during a CVVHD experiment with a porcine model.

Meropenem concentrations were determined at multiple time points during the CVVH and CVVHD experiments for each animal. As illustrated in FIGS. 22 (CVVH) and 23 (CVVHD), the clearance rate of meropenem shows a direct correlation to that of MB-102 for both CVVH and CVVHD. Using this correlation, it possible to determine the concentration of meropenem over a period of time in the bloodstream of patient based on the detected fluorescence of MB-102 and the initially administered dose of meropenem.

Figure 24:
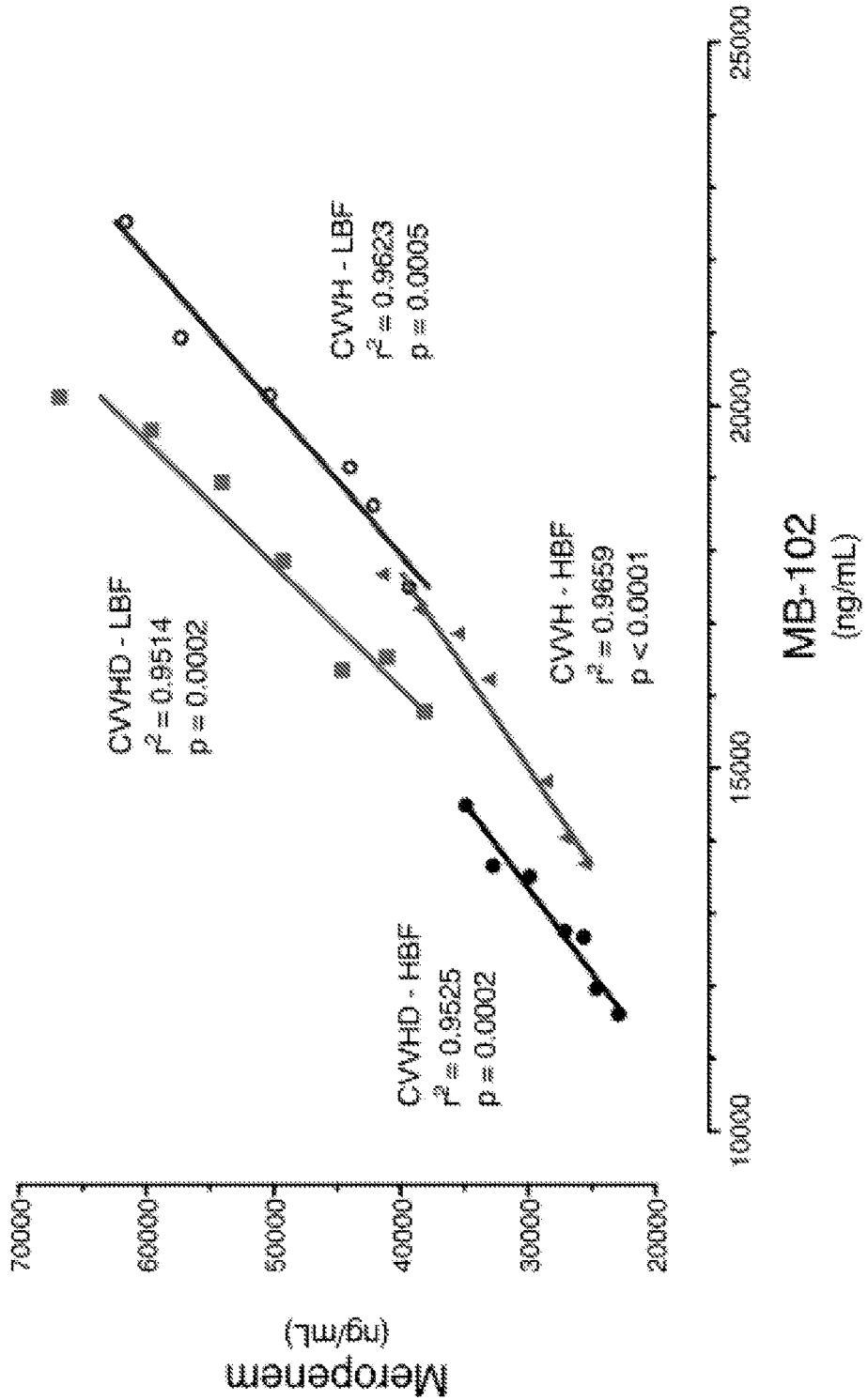
FIG. 24 is a graph that illustrates the correlation between the concentration of MB-102 and meropenem using different CRRT conditions and modalities.

As shown in Table 8 and FIG. 24, the concentration of meropenem with respect to MB-102, and thus the clearance rate, exhibits a very good linear correlation. For both CVVH and CVVHD having a low or high blood flow rate, the linear correlation coefficient ($R^2$) is greater than 0.95 with very low p-values.

TABLE 8

Statistical Analysis of MB-102 and Meropenem Clearance

| CRRT Modality | Blood Flow Rate (mL/min) | $R^2$ | P |
| --- | --- | --- | --- |
| CVVH | 100 | 0.9623 | 0.0005 |
| CVVH | 200 | 0.9659 | <0.0001 |
| CVVHD | 100 | 0.9514 | 0.0002 |
| CVVHD | 200 | 0.9525 | 0.0002 |

The written description uses examples to disclose the subject matter herein, including the best mode, and also to enable any person skilled in the art to practice the subject matter disclosed herein, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for determining a dosing prescription for a medicament in a patient undergoing continuous renal replacement therapy (CRRT), the method comprising:
    administering to the bloodstream of the patient a fluorescent agent, wherein the fluorescent agent is a compound of Formula I

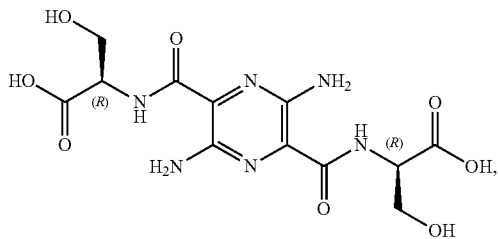

or a pharmaceutically acceptable salt thereof;
    administering to the patient at least one dose of the medicament wherein administering the fluorescent agent and the medicament to the patient is either sequential or simultaneous;
    performing CRRT on the patient after administering the fluorescent agent to the patient;
    exposing the fluorescent agent to visible or infrared light, thereby causing spectral energy to emanate from the fluorescent agent;
    monitoring transcutaneously a change in the spectral energy from the fluorescent agent over a period of time;
    correlating a change in intensity of the spectral energy from the fluorescent agent to a clearance rate of the fluorescent agent from the bloodstream in the patient;
    correlating a clearance rate of the medicament in the patient to the clearance rate of the fluorescent agent;
    determining a concentration of the medicament in the bloodstream of the patient as a function of time based on the clearance rate of the fluorescent agent; and
    adjusting the dosing prescription of the medicament to the patient based on the concentration of the medicament in the bloodstream of the patient as a function of time thereby determining the dosing prescription for the medicament to the patient.

2. The method according to claim 1, wherein the fluorescent agent is removed from the bloodstream of the patient by glomerular filtration.

3. The method according to claim 1, wherein the patient has at least one medical condition selected from the group consisting of acute kidney injury (AKI), acute renal failure, multiple organ failure, cardiac insufficiency and edema, acute pancreatitis, fulminant hepatitis, and liver failure.

4. The method according to claim 1, wherein exposing the fluorescent agent to visible or infrared light comprises:
    placing a renal monitoring assembly on a body surface of the patient; and
    wherein the renal monitoring assembly comprises a light source and a data processing system and is configured to detect spectral energy and process data indicative of the spectral energy.

5. A method for monitoring a clearance rate of a medicament in a patient undergoing CRRT, the method comprising:
    administering to the bloodstream of the patient a fluorescent agent, wherein the fluorescent agent is a compound of Formula I

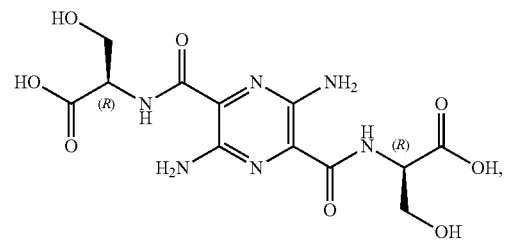

or a pharmaceutically acceptable salt thereof;
    administering to the patient at least one dose of the medicament wherein administering the fluorescent agent and the medicament to the patient is either sequential or simultaneous;
    performing CRRT on the patient after administering the fluorescent agent to the patient;
    exposing the fluorescent agent to visible or infrared light, thereby causing spectral energy to emanate from the fluorescent agent;
    monitoring transcutaneously a change in spectral energy from the fluorescent agent over a period of time;
    correlating a change in intensity of the spectral energy from the fluorescent agent to a clearance rate of the fluorescent agent from the bloodstream in the patient;
    correlating a clearance rate of the medicament in the patient to the clearance rate of the fluorescent agent; and
    determining a concentration of the medicament in the bloodstream of the patient as a function of time based on the clearance rate of the fluorescent agent thereby monitoring the concentration of the medicament in the bloodstream of the patient.

6. The method of claim 5, the method further comprising adjusting a dosing prescription of the medicament to the patient based on the concentration of the medicament in the bloodstream of the patient as a function of time.

7. The method according to claim 5, wherein the fluorescent agent is removed from the bloodstream of the patient by glomerular filtration.

8. The method according to claim 5, wherein the patient has at least one medical condition selected from the group consisting of acute kidney injury (AKI), acute renal failure, multiple organ failure, cardiac insufficiency and edema, acute pancreatitis, fulminant hepatitis, and liver failure.

9. The method according to claim 5, wherein exposing the fluorescent agent to visible or infrared light comprises:
    placing a renal monitoring assembly on a body surface of the patient; and
    wherein the renal monitoring assembly comprises a light source and a data processing system and is configured to detect spectral energy and process data indicative of the spectral energy.

10. A method for determining if a patient undergoing CRRT is receiving a therapeutically effective dose of a medicament for a therapeutically effective time period, the method comprising:

administering to the bloodstream of the patient a fluorescent agent, wherein the fluorescent agent is a compound of Formula I

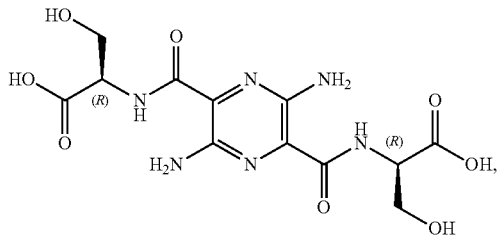

or a pharmaceutically acceptable salt thereof;
administering to the patient at least one dose of the medicament wherein administering the fluorescent agent and the medicament to the patient is either sequential or simultaneous;
performing CRRT on the patient after administering the fluorescent agent to the patient;
exposing the fluorescent agent to visible or infrared light, thereby causing spectral energy to emanate from the fluorescent agent;
monitoring transcutaneously a change in spectral energy from the fluorescent agent over a period of time;
correlating a change in intensity of the spectral energy from the fluorescent agent to a clearance rate of the fluorescent agent from the bloodstream in the patient;
correlating a clearance rate of the medicament in the patient to the clearance rate of the fluorescent agent;
determining a concentration of the medicament in the bloodstream of the patient as a function of time based on the clearance rate of the fluorescent agent thereby monitoring the concentration of the medicament in the bloodstream of the patient as a function of time; and
comparing the concentration of the medicament in the bloodstream of the patient at a specific time point to a predetermined therapeutically effective concentration thereby determining if the patient is receiving a therapeutically effective dose of the medicament for a therapeutically effective time period.

11. The method according to claim 10, wherein when the concentration of the medicament is below the predetermined therapeutically effective concentration, the method further comprises:
administering at least one additional dose of the medicament to the patient.

12. The method according to claim 10, wherein the fluorescent agent is removed from the bloodstream of the patient by glomerular filtration.

13. The method according to claim 10, wherein the patient has at least one medical condition selected from the group consisting of acute kidney injury (AKI), acute renal failure, multiple organ failure, cardiac insufficiency and edema, acute pancreatitis, fulminant hepatitis, and liver failure.

14. The method according to claim 10, wherein exposing the fluorescent agent to visible or infrared light comprises:
placing a renal monitoring assembly on a body surface of the patient; and
wherein the renal monitoring assembly comprises a light source and a data processing system and is configured to detect spectral energy and process data indicative of the spectral energy.

* * * * *

UNITED STATES PATENT AND TRADEMARK OFFICE
CERTIFICATE OF CORRECTION

| | | |
|---|---|---|
| PATENT NO. | : 12,102,432 B2 | Page 1 of 1 |
| APPLICATION NO. | : 16/552609 | |
| DATED | : October 1, 2024 | |
| INVENTOR(S) | : Stuart L. Goldstein and Richard B. Dorshow | |

It is certified that error appears in the above-identified patent and that said Letters Patent is hereby corrected as shown below:

On the Title Page

In item (73), in Assignee, delete the "," between MEDIBEACON and INC.

Signed and Sealed this
Twenty-second Day of April, 2025

Coke Morgan Stewart
*Acting Director of the United States Patent and Trademark Office*